US012678531B2

(12) United States Patent
Mori et al.

(10) Patent No.: US 12,678,531 B2
(45) Date of Patent: Jul. 14, 2026

(54) OCULAR DEVICE CASE AND REFILL CONTAINER USED FOR THE OCULAR DEVICE CASE

(71) Applicant: MENICON CO., LTD., Nagoya (JP)

(72) Inventors: Osamu Mori, Kasugai (JP); Kazuharu Niwa, Kasugai (JP); Issaku Ito, Kasugai (JP); Tomohiro Inagaki, Kasugai (JP)

(73) Assignee: MENICON CO., LTD., Nagoya (JP)

( * ) Notice: Subject to any disclaimer, the term of this patent is extended or adjusted under 35 U.S.C. 154(b) by 0 days.

(21) Appl. No.: 18/735,418

(22) Filed: Jun. 6, 2024

(65) Prior Publication Data

US 2024/0316241 A1     Sep. 26, 2024

Related U.S. Application Data

(63) Continuation of application No. 17/637,519, filed as application No. PCT/JP2019/033395 on Aug. 26, 2019, now Pat. No. 12,029,823.

(51) Int. Cl.
A61L 12/08          (2006.01)
A45C 11/00          (2006.01)

(52) U.S. Cl.
CPC .......... A61L 12/086 (2013.01); A45C 11/005 (2013.01)

(58) Field of Classification Search
CPC ..... A45C 11/005; A61L 12/086; B65D 47/06; Y10S 134/901
USPC ........... 206/5.1; 215/311; 222/211, 322, 449, 222/494, 341
See application file for complete search history.

(56) References Cited

U.S. PATENT DOCUMENTS

| | | | | |
|---|---|---|---|---|
| 2,242,876 A | * | 5/1941 | Winters | ................. A61M 11/00 |
| | | | | 222/325 |
| 3,233,727 A | | 2/1966 | Wilson | |
| 3,402,747 A | | 9/1968 | Tissot-Dupont | |
| 3,473,886 A | | 10/1969 | Leeds | |
| 3,476,507 A | | 11/1969 | Leeds | |
| 3,643,672 A | | 2/1972 | Brown | |

(Continued)

FOREIGN PATENT DOCUMENTS

| | | |
|---|---|---|
| CA | 2344683 A1 | 3/2000 |
| CN | 1130533 A | 9/1996 |

(Continued)

OTHER PUBLICATIONS

Nov. 12, 2019 Search Report issued in International Patent Application No. PCT/JP2019/033395.

(Continued)

*Primary Examiner* — Chun Hoi Cheung
(74) *Attorney, Agent, or Firm* — Oliff PLC

(57)          ABSTRACT

Provided is an ocular device case with a new structure that can solve unexpected problems in the related art, for example, adverse effects on user's eyes by splashes of treatment liquid upon pouring the treatment liquid into the device case from a separate refill container. In a device case 10 including: a case body 18 accommodating treatment liquid 12 with ocular devices such as a contact lens 16; and a lid 20, a container receiving portion 48 is provided such that a spout 106 of a refill container 100 is brought into contact with the refill receiving portion 48 so as to allow the treatment liquid 12 to flow into the device case 10.

14 Claims, 13 Drawing Sheets

(56) References Cited

U.S. PATENT DOCUMENTS

| | | | |
|---|---|---|---|
| 4,637,919 A | 1/1987 | Ryder et al. | |
| 4,672,996 A | 6/1987 | Floyd et al. | |
| 5,089,240 A | 2/1992 | Perlaky | |
| 5,127,517 A | 7/1992 | Clements et al. | |
| 5,222,522 A | 6/1993 | Rontome | |
| 5,250,266 A | 10/1993 | Kanner | |
| 5,366,078 A | 11/1994 | Braun | |
| 5,690,211 A * | 11/1997 | Jao | A45C 11/005 134/901 |
| 6,000,534 A | 12/1999 | Koomruian | |
| 6,173,851 B1 * | 1/2001 | Hague | A61J 7/003 206/370 |
| 8,122,922 B2 | 2/2012 | Baker | |
| 8,251,110 B2 * | 8/2012 | Bassett | A47K 5/12 141/319 |
| 8,459,312 B2 * | 6/2013 | Manera | B65D 47/2031 141/346 |
| 8,740,017 B2 | 6/2014 | Shibata | |
| 8,757,367 B2 | 6/2014 | Winterton et al. | |
| 8,800,759 B2 * | 8/2014 | Billiet-Prades | B65D 81/3211 141/366 |
| 2003/0057111 A1 | 3/2003 | Ichikawa et al. | |
| 2004/0251146 A1 | 12/2004 | Church et al. | |
| 2005/0126940 A1 * | 6/2005 | Nakagawa | A45C 11/005 206/316.1 |
| 2006/0248859 A1 | 11/2006 | Rosati | |
| 2010/0314418 A1 | 12/2010 | Roth et al. | |
| 2012/0251405 A1 | 10/2012 | Donley | |
| 2013/0280142 A1 * | 10/2013 | Sturm | A61L 12/08 422/292 |
| 2017/0065046 A1 | 3/2017 | Winterton et al. | |
| 2020/0229562 A1 * | 7/2020 | Almond | A45C 11/005 |
| 2022/0288269 A1 | 9/2022 | Mori et al. | |

FOREIGN PATENT DOCUMENTS

| CN | 104427904 A | 3/2015 |
|---|---|---|
| CN | 204232449 U | 4/2015 |
| CN | 208463147 U | 2/2019 |
| JP | H02-112115 U1 | 9/1990 |
| JP | H07-500425 A | 1/1995 |
| JP | H07-500426 A | 1/1995 |
| JP | H08-227058 A | 9/1996 |
| JP | 2004-290473 A | 10/2004 |
| JP | 2005-148371 A | 6/2005 |
| JP | 4306967 B2 | 8/2009 |
| JP | 2011-251246 A | 12/2011 |
| JP | 6892564 B1 | 6/2021 |
| WO | 93/09692 A2 | 5/1993 |
| WO | 2004/019114 A1 | 3/2004 |
| WO | 2014/009987 A1 | 1/2014 |

OTHER PUBLICATIONS

Mar. 1, 2022 International Preliminary Report on Patentability issued in International Patent Application No. PCT/JP2019/033395.
Apr. 28, 2023 Extended Search Report issued in European Patent Application No. 19943421.8.
Jul. 26, 2023 Office Action issued in Japanese Patent Application No. 2021-089241.
Nov. 13, 2023 Office Action issued in Chinese Patent Application No. 201980099579.2.
May 30, 2024 Office Action issued in Chinese Application No. 201980099579.2.
Nov. 15, 2024 Extended European Search Report issued in European Application No. 24192001.6.
Jul. 31, 2024 Office Action issued in Japanese Application No. 2023-210703.
Nov. 19, 2024 Office Action issued in Chinese Application No. 201980099579.2.
Jan. 24, 2025 Office Action issued in Chinese Application No. 201980099579.2.
Jan. 15, 2026 Office Action issued in Chinese Application No. 201980099579.2.

* cited by examiner

100

OCULAR DEVICE CASE AND REFILL CONTAINER USED FOR THE OCULAR DEVICE CASE

CROSS REFERENCE TO RELATED APPLICATION

This application is a continuation application of U.S. application Ser. No. 17/637,519, filed Feb. 23, 2022, the contents of which are incorporated herein by reference.

TECHNICAL FIELD

The present invention relates to an ocular device case for accommodating an ocular device such as a contact lens together with a treatment liquid, a refill container used for the ocular device case, and a treatment set for an ocular device including the same.

BACKGROUND ART

As a lens to be worn directly on the human eye, for example, a contact lens is known, but in recent years, a wider variety of lenses have been used or proposed. Specifically, for example, in addition to corrective contact lenses that correct vision such as myopia, hyperopia, presbyopia, and astigmatism, cosmetic contact lenses such as color lenses that color iris and limbal and make the cornea look larger are generally used. In addition, special contact lenses such as contact lenses that suppress the progression of myopia, contact lenses used for orthokeratology therapy, and contact lenses applied to corneal diseases such as conical keratology are also provided. Furthermore, like smart contact lenses with electronic added value, functional contact lenses that have a camera function, a communication function, an iris recognition function, a function to measure biomarkers in tears, a function to release drugs, or the like, have been also proposed. Further, intraocular lenses such as non-crystal type and crystal type that are worn in the eye are also used. Various lenses such as those worn in contact with the human eye or directly inside the human eye are generally used by being arranged on the optical path of the human eye, for example. However, some are formed with a ring shape surrounding an incident light path to the retina in order to avoid adverse influence on the visual sense. In the present specification, various devices (including those having no lens function) worn for some purpose with respect to the human eye are collectively referred to as "ocular devices".

The above-mentioned ocular device is contact with or soaked in a treatment liquid for storage, cleaning, sterilization, etc. as necessary for the purpose of storing the ocular device removed by the user or performing some treatment such as sterilization. For example, in the case of soft contact lenses and hard contact lenses that are continuously and repeatedly used, as described in Japanese Patent No. JP-B-4306967 (Patent Document 1), a contact lens case having a storage area for accommodating a treatment liquid together with a contact lens has been conventionally provided to the user.

By the way, some of the treatment liquids used in the treatment of ocular devices do not preferably touch the fingers of the user (lens user) or get into the eyes. For example, povidone iodine-based treatment liquid may cause an allergic reaction if it is not neutralized, and if the lens user is allergic to the bactericidal preservative contained in the lens cleaning liquid or preservative liquid, it is desirable to avoid contact of the user with the liquid as much as possible.

In particular, hydrogen peroxide solution and hypochlorite water used for sterilizing contact lenses cause pain when they get into the eyes even in a small amount, so it is necessary to prevent that the user contacts with the treatment liquid.

BACKGROUND ART DOCUMENT

Patent Document

Patent Document 1: JP-B-4306967

SUMMARY OF THE INVENTION

Problem the Invention Attempts to Solve

However, as a result of the examination by the present inventor, it has been found that the ocular device cases such as the contact lens cases conventionally provided or proposed have problems to be improved. That is, in the conventional ocular device case, the storage area is opened upward, and the treatment liquid is injected from the bottle-shaped treatment liquid refill container through the opening portion. There was a problem that the treatment liquid was easily scattered around. In particular, the conventional ocular device case is configured such that an ocular device like a contact lens puts in and takes out from the storage area through the upward opening portion. Thus, an opening area of the storage area is large and the treatment liquid injected from above is easily bounces off the wall surface or liquid surface of the storage area and scatters out from the opening of the storage area. Furthermore, when the treatment liquid is injected after the ocular device is set in the storage area in advance, due to the user's psychology of wanting to process the ocular device more efficiently, there is a tendency that the user injects the treatment liquid in a vigorous manner. This leads to the splashing of the treatment liquid due to the splashing of the treatment liquid by the surface of the ocular device. Thus, the splashing of the treatment liquid tends to cause a bigger problem.

Even if it is rare that the scattered treatment liquid directly enters the eyes, the scattered treatment liquid adheres directly to the fingers or adheres indirectly to the fingers when wiping off the treatment liquid adhering to the surroundings such as a table. If the users touch their eyes or wear a new ocular device with their fingers to which the treatment liquid has adhered, the treatment liquid will get into their eyes.

The present invention has been developed in view of new problems recognized from the viewpoint of use by a user, which has not been recognized in the past, such as an adverse effect on the user's eye due to the treatment liquid being scattered when the treatment liquid is injected into an ocular device case. It is an object of the present invention to provide a new ocular device case or the like that can solve at least one of the problems inherent in the conventional ocular device case by solving the new problems mentioned above and the like.

Means for Solving the Problem

Hereinafter, preferred embodiments for grasping the present invention will be described. However, each preferred embodiment described below is exemplary and can be appropriately combined with each other. Besides, a plurality of elements described in each preferred embodiment can be recognized and adopted as independently as possible, or can also be appropriately combined with any element described in other preferred embodiments. By so doing, in the present invention, various other preferred embodiments can be realized without being limited to those described below.

A first preferred embodiment provides an ocular device case that is used by injecting a treatment liquid from a separate refill container, the device comprising: a case body having a storage area for the treatment liquid; a support portion for supporting an ocular device in the storage area; a lid attached to an opening of the storage area in the case body; and a container receiving portion being configured to be brought into contact with a spout of the refill container to allow the treatment liquid to be injected into the storage area, with the ocular device being supported in the storage area by the support portion.

In the ocular device case of this embodiment, the treatment liquid can be injected from the refill container into the storage area in a state where the spout of the refill container contacts with the container receiving portion and being positioned at a predetermined site. Therefore, for example, when a user of an ocular device injects a treatment liquid from a refill container into a storage area, it is able to avoid an injection mode in which the amount of splattering of the treatment liquid tends to be large, such as vigorously injecting the treatment liquid from a position far above, or injecting the treatment liquid directly onto the device and so as to pour it vigorously over the entire surface. This makes it possible to encourage users to do an operation of injecting a treatment liquid with less splattering.

Moreover, since the treatment liquid can be injected into the storage area while the ocular device is supported in the storage area, the target treatment such as sterilization by the treatment liquid of the ocular device can be started substantially at the same time as the injection of the treatment liquid.

The second preferred embodiment provides the ocular device case according to the first preferred embodiment, wherein the container receiving portion is arranged to be contact with the spout of the refill container pointed downward from above, in an upright state of the case body to which the lid is attached.

In the ocular device case of this embodiment, the treatment liquid can be injected from the refill container into the storage area in a state where the lid is attached to the opening of the case body and there is no large opening. Therefore, it is possible to prevent the injected treatment liquid from splashing to the outside through the large opening. Further, since the refill container can be brought into contact with the case from above in the upright state of the case body for injection, for example, stable holding of the case at the time of injection and operation of injecting the treatment liquid can be more easily realized.

The third preferred embodiment provides the ocular device case according to the first or second preferred embodiment, further comprising an insertion port into which the spout of the refill container is inserted, wherein the container receiving portion is located inward of the insertion port.

In the ocular device case of this embodiment, with the spout of the refill container being positioned by the container receiving portion located inward from the insertion port in a state where the spout of the refill container is inserted into the insertion port and the insertion port is narrowed, the treatment liquid will be injected into the storage area through the opening at the tip of the spout. Therefore, even if the treatment liquid bounces off in the storage area, it can be reduced that the treatment liquid jumps out to the outside of the container and is scattered.

A fourth preferred embodiment provides the ocular device case according to the third preferred embodiment, wherein the insertion port is provided with a valve body that reduces an opening area of the insertion port in a state where the spout of the refill container is not inserted into the insertion port, rather than a state where the spout is inserted.

In the ocular device case of this embodiment, even in a state where the spout of the refill container is not inserted into the insertion port, such as a state where the ocular device is treated with a treatment liquid in the case, unnecessary opening area of the insertion port is suppressed by the valve body. Therefore, for example, the effect of suppressing the intrusion of foreign matter through the insertion port is exhibited.

A fifth preferred embodiment provides the ocular device case according to the fourth preferred embodiment, wherein the valve body comprises an elastic valve capable of increasing and decreasing the opening area of the insertion port based on elastic deformation action thereof.

In the ocular device case of this embodiment, owing to the elastic deformation action of the elastic valve, the opening of the insertion port can be made sufficiently small or substantially closed when the spout of the refill container is not inserted, while the necessary opening area is secured when the spout of the refill container is inserted, for example.

A sixth preferred embodiment provides the ocular device case according to the fourth or fifth preferred embodiment, wherein the valve body restricts a passage of the treatment liquid.

In the ocular device case of this embodiment, for example, when the spout of the refill container is not inserted, it is possible to suppress the leakage of the treatment liquid to the outside through the insertion port. When the ocular device case is moved with the treatment liquid being contained, it is also possible to prevent or suppress the careless leakage of the treatment liquid in the storage area to the outside due to vibration or the like.

A seventh preferred embodiment provides the ocular device case according to any one of the fourth through sixth preferred embodiments, wherein the valve body allow a passage of gas in a state where the spout of the refill container is not inserted.

In the ocular device case of this embodiment, for example, it is possible to prevent the internal pressure of the refill container from being unnecessarily changed due to a temperature change in the environment, or even when gas is generated from the treatment liquid contained in the treatment region, it is also possible to quickly release the generated gas to the outside.

An eighth referred embodiment provides the ocular device case according to any one of the third through seventh preferred embodiments, wherein an insertion depth of the spout of the refill container with respect to the insertion port is limited by a contact of a tip of the spout of the refill container with the container receiving portion.

In the ocular device case of this embodiment, when the user injects the treatment liquid from the refill container, the user is allowed to insert the spout of the refill container into the insertion port until the tip of the spout abuts on the container receiving portion. It becomes possible to stably specify the insertion length of the spout of the refill container with respect to the insertion port. This makes it possible to prevent or suppress that the treatment liquid leaks due to insufficient insertion depth of the spout of the refill container with respect to the insertion port, or that the insertion depth of the spout of the refill container with respect to the insertion port is too deep to interfere with the ocular device or to put an undesirable load on the valve body.

A ninth referred embodiment provides the ocular device case according to any one of the first through eighth preferred embodiments, wherein a contact position of a tip of the spout of the refill container in the container receiving portion is set above a prescript position of an liquid surface level of the treatment liquid in the storage area.

In the ocular device case of this embodiment, the spout of the refill container may be prevented from being unnecessarily contacted with the treatment liquid filled in the storage area. This makes it possible to avoid backflow of the treatment liquid filled in the storage area to the refill container. In addition, it is also possible to prevent or suppress the invasion of various germs in the treatment liquid filled in the storage area into the refill container and the transfer of germs or the like adhering to the vicinity of the spout to the treatment liquid filled in the storage area.

A tenth referred embodiment provides the ocular device case according to any one of the first through ninth preferred embodiments, wherein the treatment liquid comprises a liquid that foams during treatment with the ocular device, and a contact position of a tip of the spout of the refill container in the container receiving portion is set at a position that is equal to or below a maximum level of a level fluctuation of an liquid surface level of the treatment liquid due to foaming thereof.

In the ocular device case of this embodiment, even if the treatment liquid injected from the refill container to the treatment area remains in the container receiving portion, for example, the remained liquid can be circulated within the storage area by the treatment liquid that reaches the container receiving portion due to foaming thereof. Therefore, even if the treatment liquid remains in the container receiving portion, it is possible to avoid the problem that the remaining treatment liquid such as hydrogen peroxide solution is not neutralized and remains as an irritant or is contaminated.

An eleventh referred embodiment provides the ocular device case according to any one of the first through tenth preferred embodiments, wherein the ocular device is supported in the storage area by the support portion, and an agent acting on the treatment liquid is accommodating and arranged in the storage area of the case body with the lid being attached.

In the ocular device case of this embodiment, the treatment liquid is injected from the refill container into the storage area in a state that the ocular device is placed in the storage area where the agent acting on the treatment liquid is arranged. Specifically, in the sterilization treatment of a contact lens with a hydrogen peroxide solution, for example, it is also possible to avoid that the decomposition of the hydrogen peroxide solution by a catalyst as an agent arranged in the storage area starts at a stage before the contact lens is immersed in the solution.

A twelfth referred embodiment provides the ocular device case according to any one of the first through eleventh preferred embodiments, wherein the container receiving portion is provided with a guide flow path that guide the treatment liquid injected from the spout downward from the contact position of a tip of the spout of the refill container.

In the ocular device case of this embodiment, the treatment liquid flowing out from the spout of the refill container can be guided to a predetermined specific place set in advance by the guide flow path and filled in the storage area. Therefore, it is possible to set the flow of the treatment liquid at a place where the injection operation of the treatment liquid is less likely to scatter, and to realize a more stable injection state.

The guide flow path may be configured by, for example, a concave groove extending downward from the contact position of the tip of the spout with a downward slope, a tunnel-shaped hole, or a combination thereof. In particular, in the guide flow path having a tunnel-shaped hole, it is possible to more reliably prevent the treatment liquid from scattering around the hole by the peripheral wall of the hole. Further, the guide flow path does not have to be single and a plurality of guide flow paths may be provided, or a guide flow path in a form of splitting or merging may be adopted.

Further, it is desirable that the container receiving portion is provided with a surface-shielding portion located in front of a tip opening of the spout of the refill container in its opening direction and to which the treatment liquid flowing out from the spout and flowing toward the front in the opening direction of the spout. The momentum of the flow of the treatment liquid poured from the refill container into the storage area is large in the direction toward the front of the tip opening of the spout. Thus, suppression of the flow rate of the treatment liquid by means of the surface-shielding portion makes it possible to reduce the rebound of the treatment liquid from the liquid surface, the ocular device, the support part, etc. Further, by appropriately setting the shape of the surface-shielding portion, it is possible to guide the injected treatment liquid into the storage area while guiding it in a specific direction.

A thirteenth referred embodiment provides the ocular device case according to any one of the first through twelfth preferred embodiments, wherein a surface of the container receiving portion is coated with a water-repellent or hydrophobic surface coat.

In the ocular device case of this embodiment, the treatment liquid injected into the storage area is prevented from adhering to the container receiving portion or is swiftly flowed downward after adhering. This makes it possible to avoid that the treatment liquid adheres to and remains in the container receiving portion. Therefore, this embodiment is effective to solve the problems such that the treatment liquid adhering to the container receiving portion is evaporated and a specific component may be increased, or that the hydrogen peroxide solution as the treatment liquid may remain without being decomposed by the catalyst.

A fourteenth preferred embodiment provides the ocular device case according to any one of the first through thirteenth preferred embodiments, wherein the case body includes an opening that opens the storage area upward, the lid is attached to the opening, and the lid is provided with the support portion that is inserted into the storage area from the opening, while the lid is provided with an insertion port into which the spout of the refill container is inserted, the container receiving portion being provided to be positioned below the insertion port and above a support position of the ocular device by the support portion in an upright state of the case body to which the lid is attached.

In the ocular device case of this embodiment, the structure of the container body can be simplified by providing the support portion and the insertion port. In addition, the insertion port is provided on the lid and the insertion port does not function unless the lid is attached to the container body. Thus, this arrangement makes it possible to guide the user easily and precisely perform a series of processes of attaching the lid to the case body after the ocular device being supported by the support portion provided in the lid, and then injecting the treatment liquid from the spout into the storage area to fill the storage area. Further, the position of the container receiving portion in the upright state of the case body to which the lid is attached is set below the insertion slot and above the support position of the ocular lens. Therefore, when the user injects the treatment liquid, the spout of the refill container can be easily positioned by the insertion slot, and it is also easy to avoid the spout inadvertently interfering with the ocular device.

A fifteenth preferred embodiment provides the ocular device case according to any one of the first through fourteenth preferred embodiments, wherein the treatment liquid comprises any one of the following [1], [2], and [3], and is used for a purpose of disinfecting or cleaning the ocular device: [1] a peroxide selected from hydrogen peroxide, perboric acid, peracetic acid, performic acid, and salts thereof; [2] an oxide of chlorine selected from chlorine dioxide, chlorite, hypochlorite, and salts thereof; and [3] Povidone Iodine.

The ocular device case of this embodiment is capable of reducing inadvertently scattering of the treatment liquid to the outside of the case, when the user of the ocular device performs sterilization, disinfection, cleaning, etc. of the ocular device by using hydrogen peroxide solution or the like as a treatment liquid that causes great irritation when it enters the eye. Therefore, the risk of eye irritation by the scattered treatment liquid through the fingers may be reduced.

A sixteenth preferred embodiment provides the ocular device case according to any one of the first through fifteenth preferred embodiments, wherein the ocular device comprises: a contact lens for vision correction such as myopia, hyperopia, and presbyopia; a cosmetic contact lens such as iris coloring and limbal dilation; a special contact lens such as a myopia suppression contact lens, an orthokeratology contact lens; a contact lens for conical corneal; a functional contact lens equipped with sensors, communication functions, imaging functions, etc.; and an intraocular lens such as a non-crystal type or a crystal type.

For various ocular lenses (including those having no optical action such as refraction), the ocular device case of this embodiment can be provided for distribution, storage, sterilization, and the like, in various mode that meet each of types of ocular lenses, each need of each user such as specialists and general users. For instance, as a refill container for injecting the treatment liquid, an individual small-capacity bottle type used by general users is adopted, and a large-capacity tank type including the treatment liquid supply line used by the manufacturer on the production line is adopted.

A seventeenth preferred embodiment provides an ocular device case that is used by injecting a treatment liquid from a separate refill container, the device comprising: a case body having a storage area for the treatment liquid; a support portion for supporting an ocular device in the storage area; and a lid attached to an opening of the storage area in the case body, wherein the case is arranged to allow pouring the treatment liquid into the storage area in a state where the case body is closed by the lid.

In the ocular device case of this embodiment, the treatment liquid can be poured and injected from the refill container into the storage area with the lid being attached to the opening of the case body and having no large opening. Therefore, it is possible to prevent the treatment liquid that has flowed into the storage area from scattering to the outside through the large opening, and it is possible to induce the user to perform the injection operation of the treatment liquid with less scattering.

A eighteenth preferred embodiment provides a refill container that is used in combination with the ocular device case according to any one of the first through seventeenth preferred embodiments, and that contains the treatment liquid to be injected into the ocular device case, the refill container comprising: a spout through which the treatment liquid flows out; and a shutoff valve body having a protrusion protruding outward from a tip of the spout; wherein the shutoff valve body is assembled in the spout such that the shutoff valve body is urged from an inside toward an outside of the spout with the protrusion protruding outward to block the spout, and with the protrusion at the spout being brought into contact with the container receiving portion of the ocular device case and pushed inward, the spout opens to allow the treatment liquid to flow out from the spout.

In the refill container of this embodiment, the treatment liquid can be discharged by opening the spout by pressing the protrusion protruding from the tip of the spout against the container receiving portion. Therefore, by pressing the tip of the spout of the refill container against the container receiving portion, the refill container can be stably positioned with respect to the ocular device case and the treatment liquid can be injected. Further, when the treatment liquid is injected into the ocular device case, the container receiving portion is positioned in front of the spout in its opening direction. Therefore, the treatment liquid flowing out vigorously from the spout of the refill container toward the front in the opening direction is likely to hits the container receiving portion, so that the treatment liquid is dispersed and the flow velocity is reduced. This makes it possible to reduce the scattering of the treatment liquid to the outside due to the rebound.

A nineteenth preferred embodiment provides a treatment set with a treatment liquid for an ocular device, wherein the ocular device case according to any one of the first through seventeenth preferred embodiments and the refill container according to the eighteenth embodiment are adopted in combination.

The treatment set having a structure according to this embodiment makes it possible to provide general users with a refill container having a spout appropriately matched to a container receiving portion provided in a ocular device case in combination with the ocular device case. In particular, the refill container according to the eighteenth preferred embodiment is adopted. This makes it possible to prevent unintentional outflowing of the treatment liquid from the spout of the refill container away from the ocular device case, when the treatment liquid is injected into the ocular device case, for example, at the stage where the spout of the refill container is pressed by the container receiving portion of the ocular device case, or at the stage where the refill container is away from the ocular device case after injection. Namely, since the outlet of the treatment liquid in the refill container, i.e., the spout, is closed by the shutoff valve body, the treatment liquid does not unintentionally spill just by tilting the refill container.

In addition, by adopting a refill container equipped with a shutoff valve body, there is an advantage that it can be effectively prevented from being mistakenly used as a rinsing solution for an ocular device. That is, the rinse solution of the ocular device is generally used so as to pour directly onto the ocular device from the spout of the container facing downward. Thus, it is difficult to use if there is a shutoff valve body that does not allow the treatment liquid to flow out without being pushed the protrusion protruding from the spout into inside. Therefore, by providing a shutoff valve in a refill container for a treatment liquid such as a cleaning liquid or a disinfectant that is not suitable for a rinsing liquid, even if the container is turned upside down and pressed against the peripheral wall of the container in order to mistakenly use for rinsing the treatment liquid contained in the refill container. Thus, it is also possible to prevent misuse of the treatment liquid by the user who does not assume filling the storage area of the ocular device case with the treatment liquid.

Effect of the Invention

According to the present invention, a new problem that has not been recognized in the past can be proposed. That is, there is a problem caused by the treatment liquid being scattered when the treatment liquid is injected into an ocular device case, for example. In response to this new problem, according to the ocular device case and the like according to each of the above-described embodiments, it is possible to suppress the scattering of the treatment liquid injected into the storage area due to the splashing to the outside. It is also possible to encourage the user to perform the injection operation of the treatment liquid with a smaller amount of scattering.

EMBODIMENTS FOR CARRYING OUT THE INVENTION

Hereinafter, practical embodiments of the present invention will be described with reference to the drawings.

Figure 1:
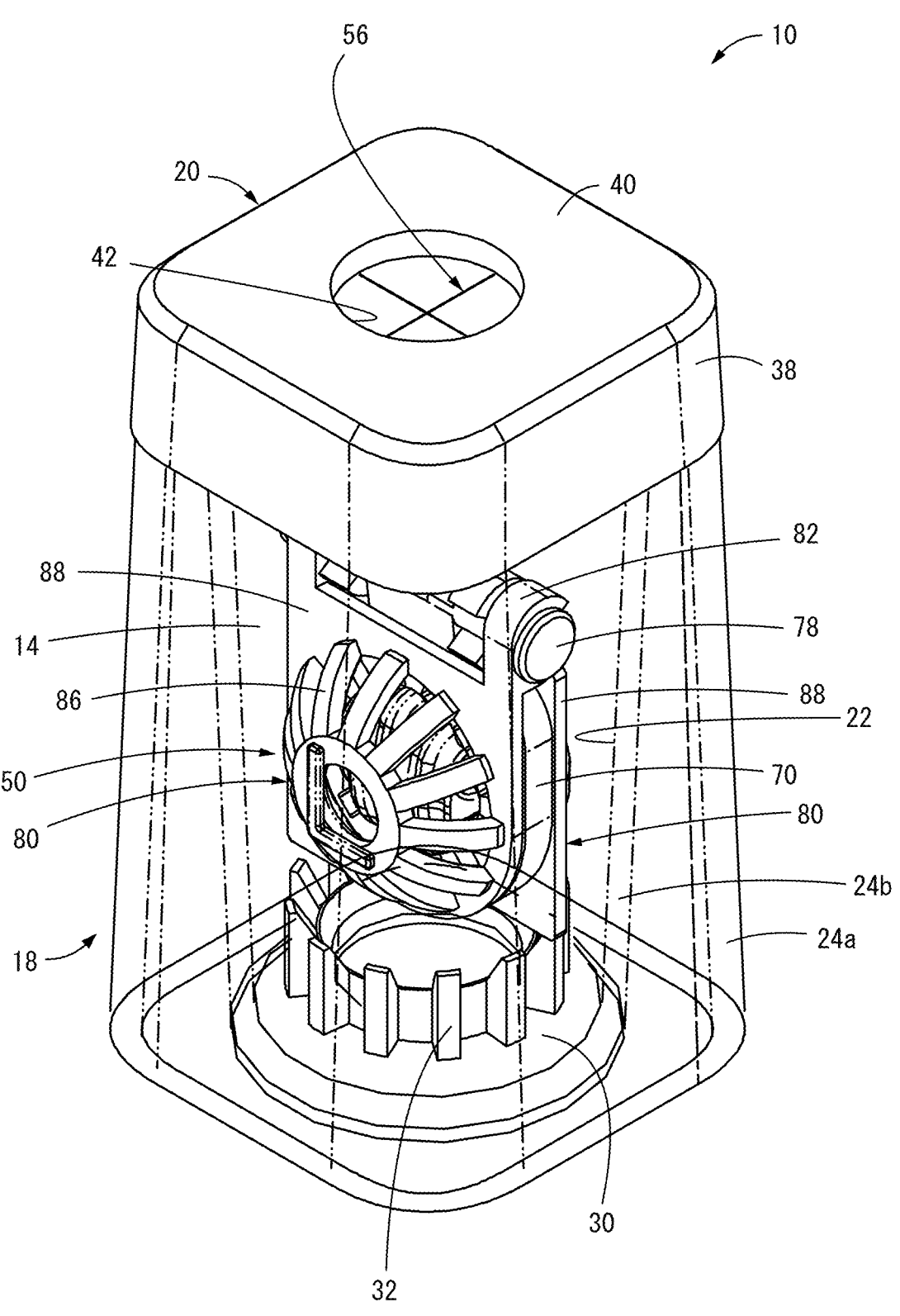
FIG. 1 is a whole perspective view of a lens case as one embodiment of the present invention.
Figure 2:
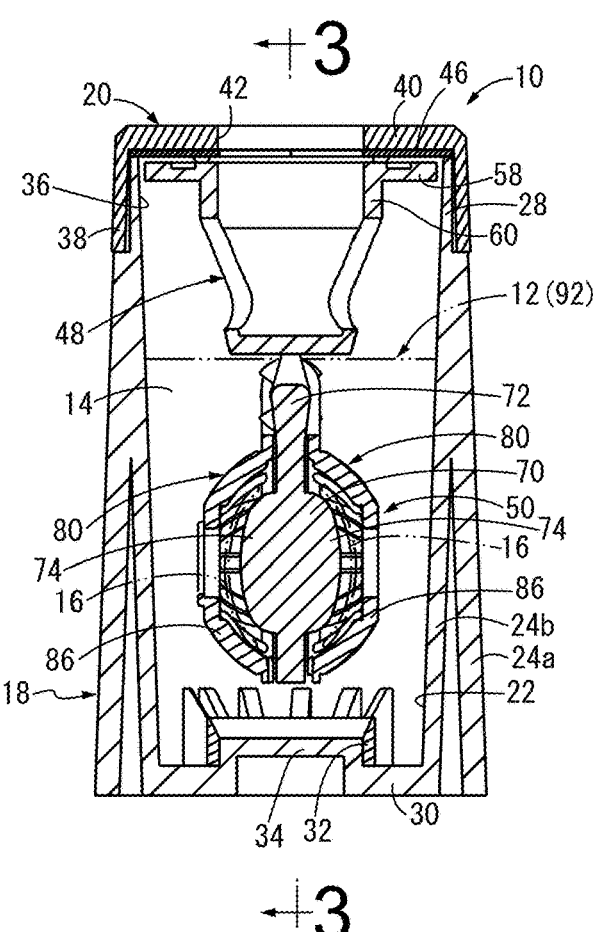
FIG. 2 is a vertical cross sectional view of the lens case of FIG. 1.
Figure 3:
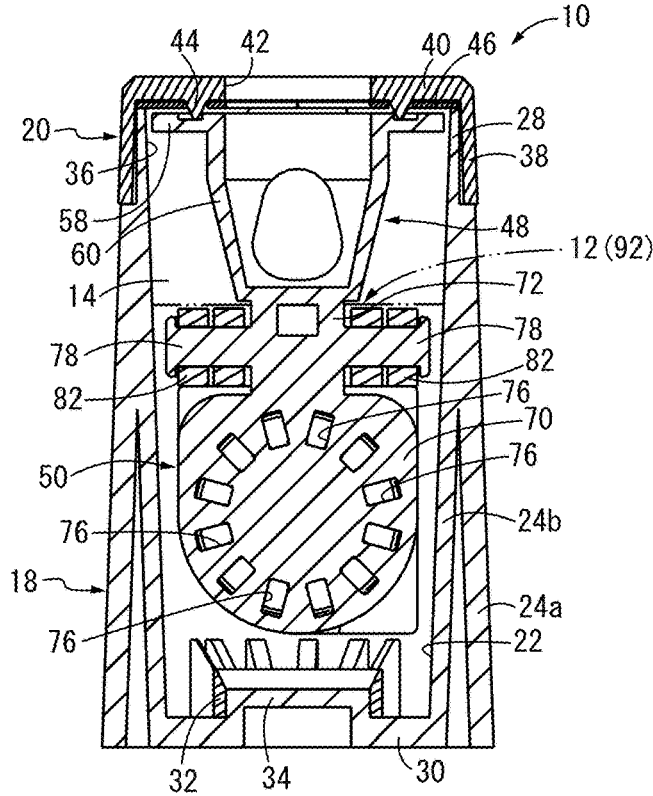
FIG. 3 is a sectional view taken along line 3-3 of FIG. 2.
Figure 4:
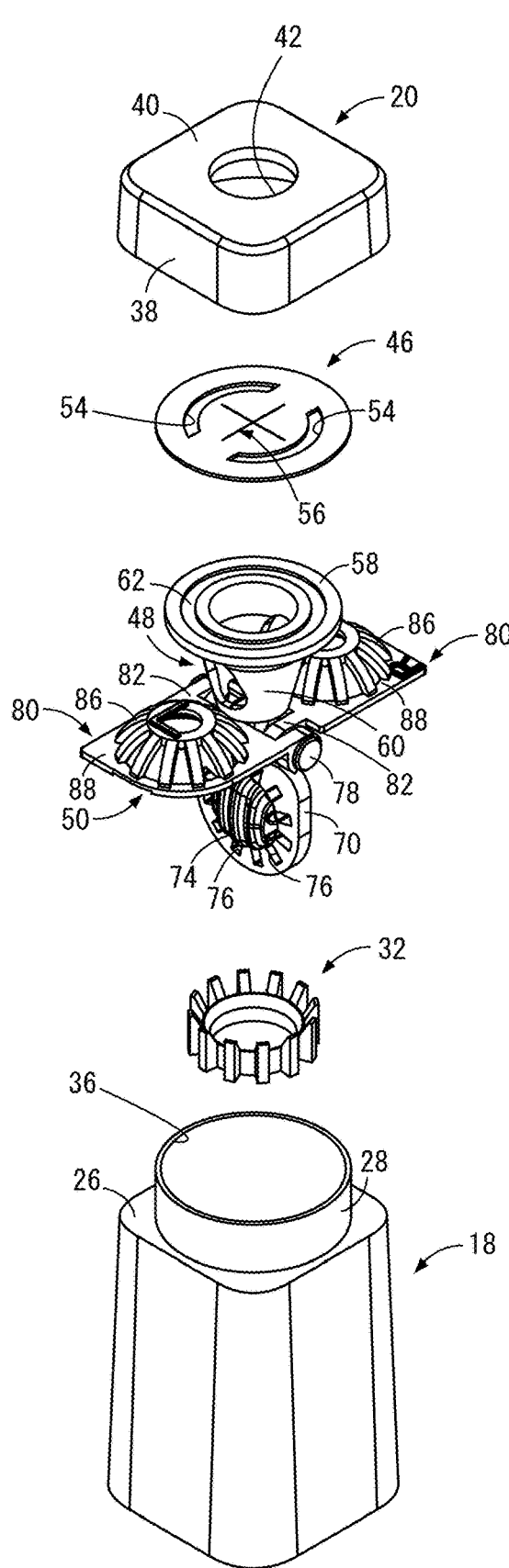
FIG. 4 is an exploded perspective view of the lens case of FIG. 1 from diagonally above.
Figure 5:
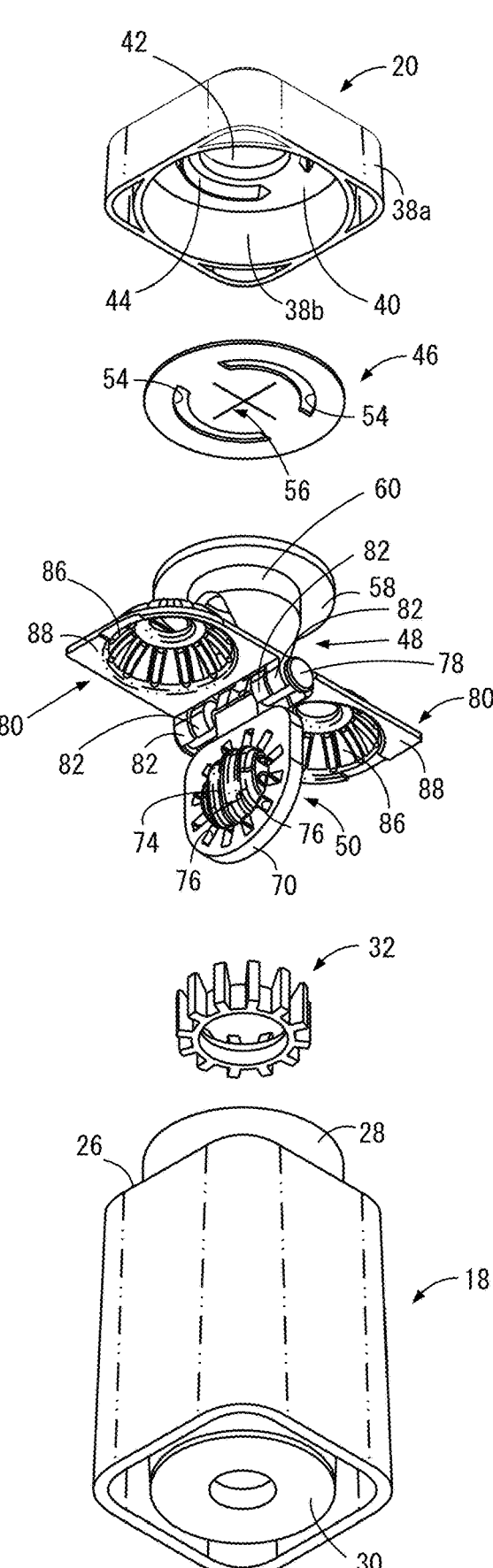
FIG. 5 is an exploded perspective view of the lens case of FIG. 1 from diagonally below.

FIG. 1 shows a lens case 10 for a contact lens, which is an embodiment of the present invention relating to an ocular device case. FIGS. 2 and 3 show a vertical cross sectional view of the lens case 10, and FIGS. 4 and 5 show exploded perspective views of the lens case 10.

The lens case 10 of the present embodiment has an storage area 14 for accommodating a treatment liquid 12, and by holding contact lenses 16 and 16 in an immersed state in the storage area 14, the contact lenses 16 and 16 are subjected to a predetermined treatment performed with the treatment liquid 12. In the following explanation, an up-down direction is, in principle, a vertical direction, and is the vertical direction in FIGS. 2 and 3 where the contact lens case 10 is shown in an upright state in which the bottom surface of the contact lens case 10 is placed on a horizontal support surface such as a table.

Further, the treatment liquid 12 is not limited in the present invention, and may be, for example, a storage liquid that is used to perform a storage treatment on the contact lens 16. In the present embodiment, hydrogen peroxide water is used as the treatment liquid. By adopting hydrogen peroxide water, it is possible to provide a lens case 10 for contact lens disinfection capable of subjecting the contact lens 16 to a disinfection treatment including sterilization.

More specifically, the lens case 10 of the present embodiment includes a case body 18 and a lid 20. The case body 18 is formed with a storage recess 22 that defines the storage area 14. The storage recess 22 is opened upward with a depth and a size capable of storing a predetermined amount of the treatment liquid 12 and holding the pair of contact lenses 16 and 16 in the immersed state.

The material of the case body 18 and the lid 20 is not limited, but is preferably molded using a synthetic resin material such as polyethylene terephthalate, polypropylene, polystyrene, or ABS. Further, by making the case body 18 transparent or translucent, the treatment liquid 12 and the contact lenses 16 contained therein can be visually recognized from the outside. In FIG. 1, it is assumed that the case body 18 is transparent, and in addition to the external structural line of the case body 18 to be seen, the internal inclusions to be seen through are also shown by solid lines.

The case body 18 of the present embodiment has a peripheral wall 24. The peripheral wall 24 includes an outer peripheral wall 24a having a substantially rectangular tubular shape and extending vertically, and an inner peripheral wall 24b having a substantially circular tubular shape extending vertically. The outer peripheral wall 24a is slightly widened downward, while the inner peripheral wall 24b is slightly widened upward. The outer peripheral wall 24a and the inner peripheral wall 24b are integrated at the upper part, while a gap is set between the peripheral walls at the lower part. Further, at the upper end portion of the case body 18, the inner peripheral wall 24b projects upward from the outer peripheral wall 24a. An upper end surface of the outer peripheral wall 24a defines a stepped surface 26, and a portion of the inner peripheral wall 24b projecting upward from the stepped surface 26 having a cylindrical shape with a substantially constant outer diameter dimension provides a lid fitting portion 28.

Further, the lower end of the inner peripheral wall 24b is closed by providing a bottom wall 30. As a result, a storage area 14 for storing the treatment liquid 12 is formed inside the case body 18 as a concave space surrounded by the inner peripheral wall 24b and opening upward. In consideration of being used as a lens case 10 for disinfection, the case body 18 of the present embodiment has a catalyst 32 serving as an agent arranged in the storage area 14, for acting on the hydrogen peroxide solution used as the treatment liquid 12 to neutralize within a predetermined time. The catalyst 32 has a ring shape similar to a crown having irregularities in order to secure a contact area with the treatment liquid 12, and is externally fixed to an inward convex portion 34 formed in the central portion of the bottom wall 30 of the case body 18. Thus, the catalyst 32 is installed at the bottom of the storage area 14.

Figure 6:
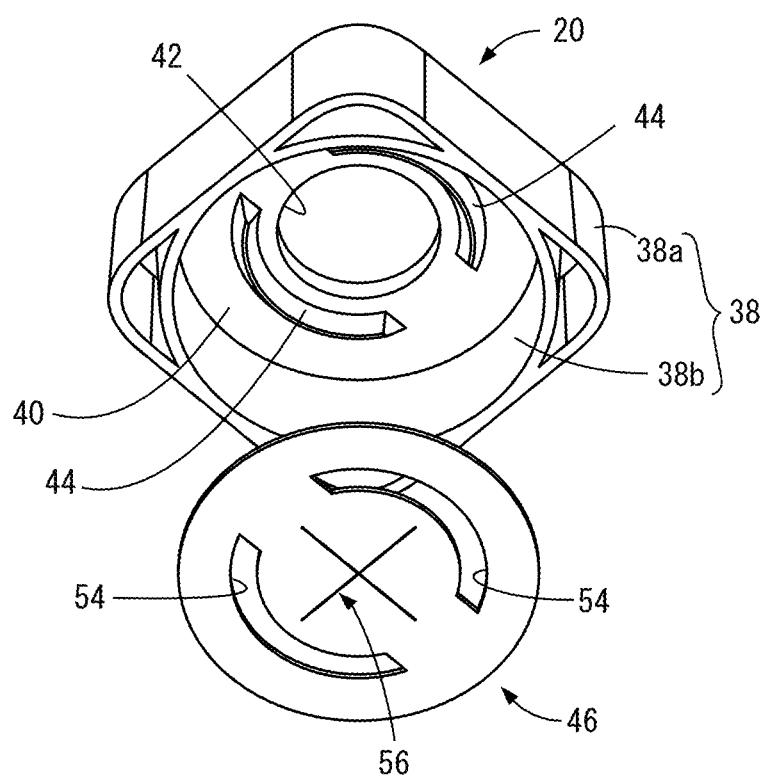
FIG. 6 is an exploded perspective view of a lid of the lens case of FIG. 1 from diagonally below.

The lid 20 has a shallow-bottomed cap structure that opens downward, and is fitted so as to cover the lid fitting portion 28 of the case body 18 from above so as to cover an opening 36 at the upper end of the storage area 14. As shown in FIG. 6, a peripheral wall 38 of the lid 20 includes: a substantially square cylindrical outer peripheral wall 38a corresponding to the outer peripheral wall 24a of the case body 18; and a substantially cylindrical inner peripheral wall 38b corresponding to the inner peripheral wall 24b of the case body 18. The inner peripheral wall 38b has a diameter dimension inscribed in the outer peripheral wall 38a, and is integrated with the outer peripheral wall 38a at four points in the circumferential direction. The outer peripheral wall 38a and the inner peripheral wall 38b are integrally molded including a flat plate-shaped upper bottom wall 40.

In the present embodiment, the outer peripheral surface of the lid fitting portion 28 of the case body 18 and the inner peripheral surface of the inner peripheral wall 38b of the lid 20 are brought into contact with each other to be fitted together, whereby the lid 20 can be attached to and detached from the case body 18. Alternatively, the lid 20 may be attached to and detached from the case body 18 with a screw structure, for example.

Further, an insertion port 42 is formed in the upper bottom wall 40 of the lid 20 so as to penetrate the central portion. A spout for a refill container which will be described later, is inserted into the insertion port 42. On the outer peripheral side of the insertion port 42, there is integrally formed a fixing protrusion 44 protruding downward from the upper bottom wall 40 having an arc shape extending in the circumferential direction at the diametrical intermediate portion between the insertion port 42 and the inner peripheral wall 38b. In the present embodiment, a pair of fixing protrusions 44, 44 having a circumferential length less than half the circumference are formed so as to face each other in the diametrical direction.

A packing 46 constituting the valve body and a holder member 52 with a receiving portion are sequentially overlapped with respect to the lid 20 from below. The holder member 52 includes a container receiving portion 48 and a support portion 50 in combination. It is fixed to the upper bottom wall 40 of the lid 20 by using the pair of fixing protrusions 44, 44.

The packing 46 has a circular plate shape, and is formed of an elastic plate made of an elastomer such as silicone or rubber. The outer diameter of the packing 46 is slightly smaller than the inner diameter of the inner peripheral wall 38b of the lid 20, is fitted into the inner peripheral wall 38b, and is overlapped with the lower surface of the upper bottom wall 40 of the lid 20. Further, the packing 46 is formed with a pair of positioning holes 54, 54 at positions corresponding to the pair of fixing protrusions 44, 44 on the lid 20 having an arc shape corresponding to the fixing protrusions 44, 44. When the packing 46 is superposed on the lower surface of the upper bottom wall 40 of the lid 20, the fixing protrusions 44, 44 of the lid 20 are fitted into the positioning holes 54, 54 and penetrate the positioning holes 54, 54 so as to protrude downward.

Further, a slit 56 is formed in the central portion of the packing 46. The specific shape of the slit 56 is not limited, and for example, a single-character slit, three or more radial slits, or the like can be adopted. In the present embodiment, the cross-shaped slit 56 composed of two orthogonal slits is adopted. The slit 56 is formed so as to avoid the formed portion of the positioning holes 54, 54. In the present embodiment, the slit 56 is located on the inner peripheral side of the circle on which the positioning holes 54, 54 are located. The slit 56 is provided with a size extending to a region substantially the same as or slightly larger than the internal region of the insertion port 42.

The slit 56 can have a slit structure having substantially no width by cutting the slit 56 with a cutter or the like after the packing 46 is formed, and can be held in a substantially closed state by the elasticity of the packing 46. On the other hand, in the central portion of the packing 46, elastic deformation such that the packing 46 is rolled up and opened in the vertical direction is easily generated by a force applied from the outside so that the slit 56 can be opened. Moreover, the slit 56 can be restored to the initial closed state by elasticity by removing the external force.

Since the packing 46 is superposed on the lower surface of the upper bottom wall 40 of the lid 20, the insertion port 42 of the lid 20 is covered with the packing 46 from the inside. The packing 46 functions as an elastic valve of the insertion port 42, so that the slit 56 is expanded by the spout of the refill container to be inserted from the insertion port 42 to be in a communicating state. Alternatively, it may be possible to release the oxygen gas generated by the decomposition of the hydrogen peroxide solution described later, since the slit 56 is expanded by the internal pressure of the storage area 14.

Figure 7:
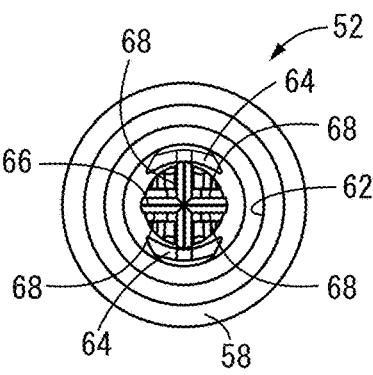
FIG. 7 shows outline views showing a support portion of the lens case of FIG. 1 shown in FIG. 1 from four directions in total, i.e., a front view, a side view, a top view and a bottom view.
Figure 7:
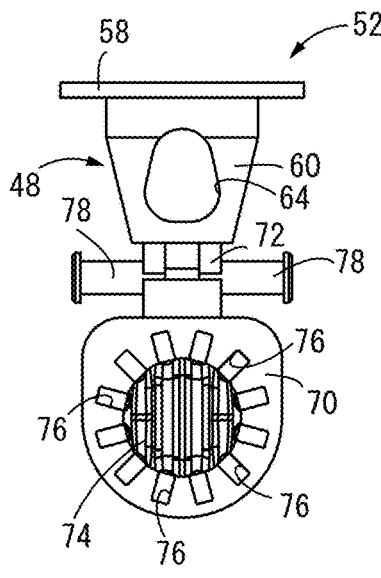
Figure 7:
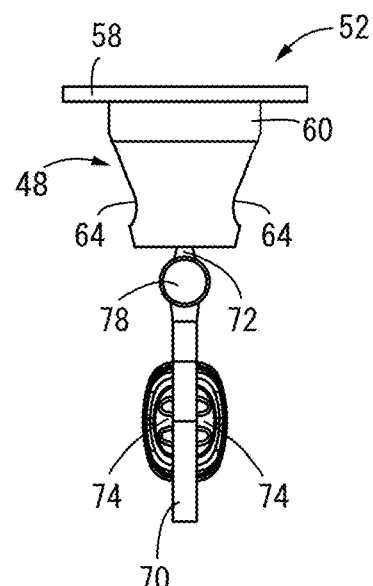
Figure 7:
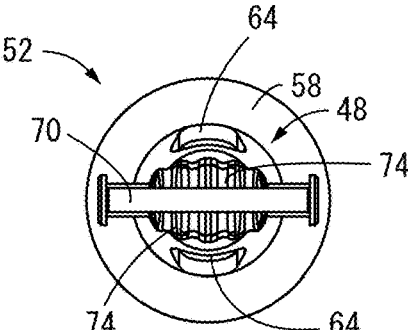
Figure 8:
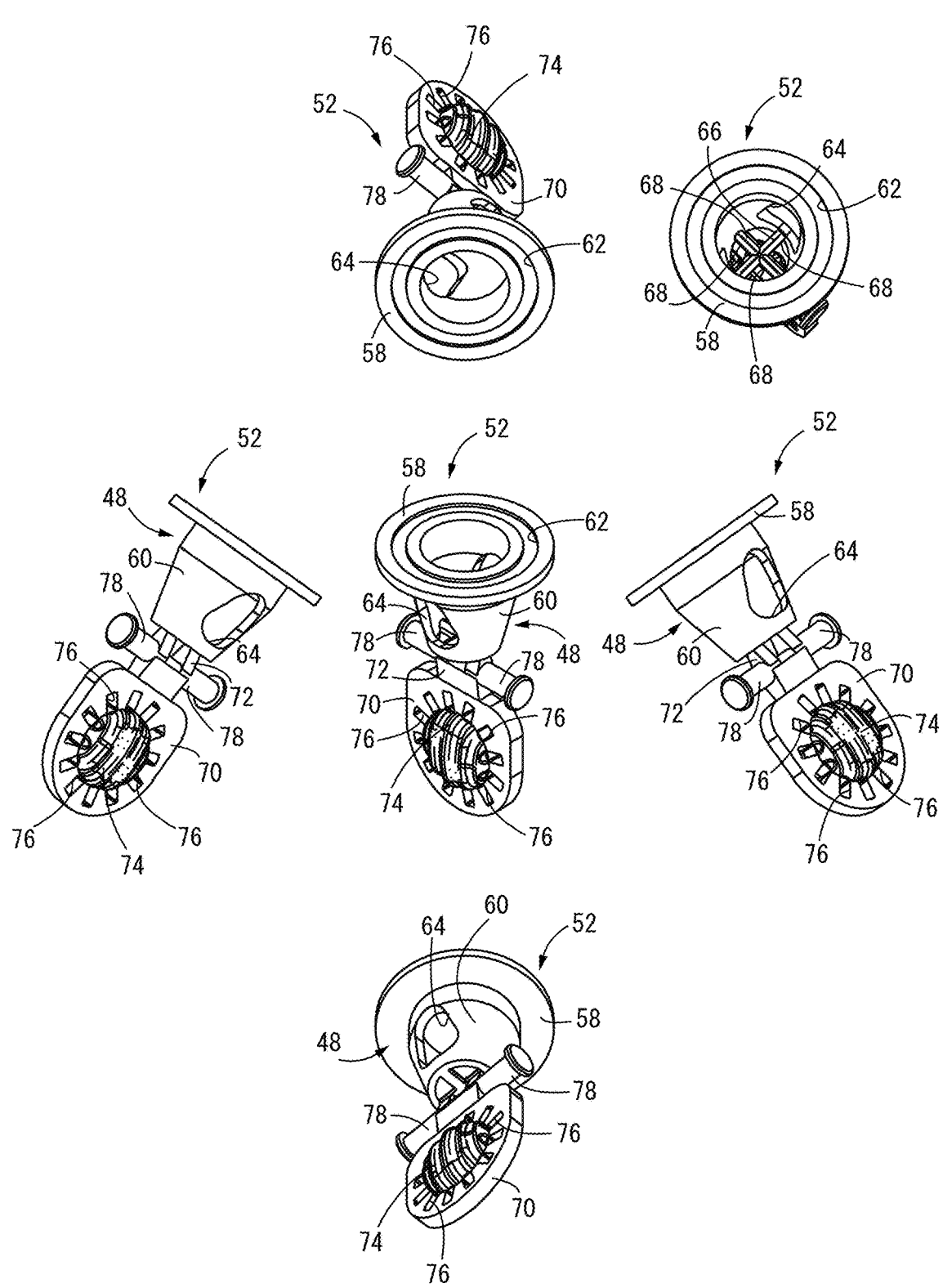
FIG. 8 shows perspective views from 6 directions in total of the support portion of FIG. 7.

Further, the holder member 52 with a receiving portion is assembled to the lid 20 from further below the packing 46. As shown in the single item state in FIGS. 7 and 8, the holder member 52 with a receiving portion has the container receiving portion 48 for receiving a spout of a refill container, which will be described later, which is inserted through the insertion port of the lid 20. At the same time, the support portion 50 that is located below the container receiving portion 48 and holds the pair of contact lenses 16 and 16 in a housed state is provided integrally with the container receiving portion 48.

The container receiving portion 48 has a substantially funnel-shaped tubular shape having a smaller diameter downward, and a flange-shaped portion 58 extending to the outer periphery at the opening peripheral edge is integrally formed at the upper end of the container receiving portion 48. The inner diameter of the upper end of the peripheral wall 60 of the container receiving portion 48 is substantially equal to the inner diameter of the insertion port 42 of the lid 20, and the outer diameter of the flange-shaped portion 58 is slightly smaller than the inner diameter of the inner peripheral wall 38b of the lid 20.

The flange-shaped portion 58 is overlapped with the lower surface of the upper bottom wall 40 of the lid 20 with the packing 46 interposed therebetween, and is fixedly attached. The fixing structure between the lid 20 and the container receiving portion 48 is not limited. For example, a fixing structure by screwing can be adopted. In the present embodiment, the lid 20 and the container receiving portion 48 are fixed by fixing the protruding tips of the fixing protrusions 44, 44 of the lid 20 protruding downward while penetrating the positioning holes 54 and 54 of the packing 46, to the upper surface of the flange-shaped portion 58.

In the present embodiment, a peripheral groove 62 is formed on the upper surface of the flange-shaped portion 58 so as to continuously extend the radial intermediate portion over the entire circumference, and the protruding tip portions of the fixing protrusions 44 and 44 of the lid 20 are in contact with the bottom surface of the peripheral groove 62 and is fixed by welding with ultrasonic waves or high frequencies. Therefore, burrs and the like due to welding are also accommodated in the peripheral groove 62, and adverse effects of the burrs against the packing 46 are avoided. In the drawings of FIGS. 2 and 3, the fixing protrusion 44 is shown at the initial height of the tapered shape for convenience during drawing, but it is actually fixed by being crushed by the welding process. The height dimension of the protrusion 44 is the same as or smaller than the thickness dimension of the packing 46, whereby it is desirable that the packing 46 is sandwiched between the upper bottom wall 40 of the lid 20 and the flange-shaped portion 58 of the container receiving portion 48 in a compressed state over a wide area including the periphery of the fixing protrusion 44.

In addition to the outer peripheral portion of the packing 46 being sandwiched and supported by a wide annular region between the upper bottom wall 40 of the lid 20 and the flange-shaped portion 58 of the container receiving portion 48, the fixing protrusions 44, 44 are fitted into the positioning holes 54, 54 of the packing 46. As a result, the packing 46 is accurately positioned at the time of assembly, and misalignment and twisting after assembly are effectively prevented. Thus, the stable support state of the packing 46 is more reliably maintained, with respect to an external force applied upon insertion of the spout of the refill container, which will be described later.

Further, a peripheral wall 60 of the container receiving portion 48 has a substantially cylindrical shape with a taper in which the lower portion has a larger inclination angle than the upper portion. Further, the peripheral wall 60 is formed with a side window 64 that penetrates inside and outside in the lower portion having a large inclination angle. In this embodiment, a pair of side windows 64, 64 are formed so as to face each other in the diametrical direction. However, the positions, numbers, sizes, etc. of the side windows 64, 64 are not limited.

A lower window 68 penetrating vertically is formed on a bottom wall 66 of the container receiving portion 48. In the present embodiment, a total of four fan-shaped lower windows 68 having a size less than each quarter circumference around the center of the substantially disk-shaped bottom wall 66 are formed evenly in the circumferential direction. With these four lower windows 68, the bottom wall 66 has a grid shape extending in a cross shape in a plan view. It should be noted that the portion of the bottom wall 66 having a grid shape may have a cross-sectional shape such that the top portion (tip end portion) has almost no width and the width dimension expands downward, for example, a substantially triangular shape. This makes it possible to prevent the treatment liquid from staying on the bottom wall 66.

A holder base 70 is integrally provided below the container receiving portion 48. The holder base 70 has a substantially small hook-shaped plate shape having a linear upper end edge and a semicircular lower portion. The holder base 70 is supported by a connecting portion 72 projecting downward from the bottom wall 66 of the container receiving portion 48, in a state of spreading substantially up, down, left and right. The holder base 70 has an outer peripheral shape that is one size larger than that of the contact lens 16, and each of the central portions on both sides is provided with a ball-shaped holding convex portion 74 that protrudes outward.

A plurality of rib-shaped protrusions extending vertically are formed on the surface of each holding convex portion 74. Further, on the outer peripheral side of the holding convex portion 74, a plurality of communication holes 76 are formed in the circumferential direction through the holder base 70. This prevents the contact lens 16 from sticking to the holding convex portion 74, and improves the contact and circulation performance of the treatment liquid with the concave rear surface of the contact lens 16.

Further, a pair of support shafts 78, 78 located above the holder base 70 and projecting substantially parallel to the upper end edge of the holder base 70 are formed in the vertical intermediate portion of the connecting portion 72. The support shafts 78 and 78 have a rod shape with a circular cross section. As shown in FIGS. 4 and 5, the holder caps 80 and 80 overlapped on both sides of the holder base 70 are assembled so as to be openable and closable by the support shafts 78 and 78.

The holder cap 80 has a spherical cap-shaped mesh portion 86 having a central portion bulging outward, and an annular plate portion 88 having a flat outer peripheral portion. Further, a pair of C-shaped hooks 82, 82 are provided on the upper end edge of the holder cap 80, and the hooks 82, 82 are externally fitted to the support shafts 78, 78 of the holder base 70. The holder cap 80 is rotatably assembled around the support shaft 78 with respect to the holder base 70 over approximately 90 degrees or more.

By rotating around the support shaft 78, each holder cap 80 can be moved with respect to each one surface of the holder base 70, from the superposed closed state as shown in FIG. 2 to the open state that opens upward as shown in FIGS. 4 and 5.

In a state where the holder cap 80 is rotated downward and superposed on the surface of the holder base 70, as shown in FIG. 2, the flat annular plate portion 88 of the holder cap 80 is held in contact with or is close and superposed to a flat outer circumference of the holder base 70. The spherical cap-shaped mesh portion 86 of the holder cap 80 is overlapped so as to cover the holding convex portion 74 of the holder base 70 from the outside at a predetermined distance. As a result, a holding region for holding the contact lens 16 is formed between the holder base 70 and the holder cap 80. In short, in the present embodiment, the support portion 50 that supports the contact lens 16 is configured including the holder base 70 and the holder cap 80.

It is desirable that the holding region of the contact lens 16 is formed with a size and shape that can hold the contact lens 16 without compression or deformation. In a state where the contact lens 16 is accommodated and held in the holding region, the convex front surface of the contact lens 16 is covered with the holder cap 80. Since the holder cap 80 has a mesh structure, the contact lens 16 is prevented from sticking to the holder cap 80, and the contact and circulation performance of the treatment liquid 12 with the contact lens 16 is ensured. On the other hand, the holding region can be opened by rotating the holder cap 80 upward around the support shaft 78 to open the holder cap 80, and in such an opened state, the contact lens 16 can be taken in and out of the holding region.

By fixing the holder member 52 with a receiving portion to the lower surface of the upper bottom wall 40 of the lid 20, the container receiving portion 48 and the support portion 50 are positioned below the lid 20 in a state of being sequentially arranged downward on substantially the same central axis as the insertion port 42. When the lid 20 is attached to the upward opening 36 of the case body 18, the holder member 52 with a receiving portion is placed in a state where the holder caps 80, 80 are closed and overlapped with the holder base 70, and is inserted into the storage recess 22 from the lower end side through the opening 36. In a state where the lid 20 is attached to the lid fitting portion 28 of the case body 18, the storage recess 22 is covered with the lid 20 to define the storage area 14, and the container receiving portion 48 and the support portion 50 are positioned and arranged in a central portion separated from the peripheral wall 24 (inner peripheral wall 24b) radially inwardly. That is, the support portion 50 for accommodating and holding the contact lenses 16, 16 is arranged in the storage area 14 in a state of being suspended from the lid 20 via the connecting portion 72 and the container receiving portion 48.

In the storage area 14, a prescript liquid surface level 92 of the stored treatment liquid 12 is set to a depth at which the support portion 50 can be immersed. Preferably, as illustrated in FIGS. 2 and 3, the prescript liquid surface level 92 is set such that the treatment liquid 12 is positioned below the upper surface of the bottom wall 66 of the container receiving portion 48 and substantially on the connecting portion 72 in the mounted state of the lid 20. As a result, it is possible to prevent the treatment liquid 12 such as hydrogen peroxide solution injected from the refill container, which will be described later, from accumulating on the bottom wall 66 and remaining without being decomposed by the action of the catalyst 32.

The holder member 52 with a receiving portion is desirable to be coated, by being subjected to a surface-treatment or a surface-working, so as to impart water repellency or hydrophobicity, particularly on the container receiving portion 48 or the like located above the prescript liquid surface level 92 of the treatment liquid 12. This makes it possible to suppress the adhesion of the treatment liquid 12. The water-repellent or hydrophobic surface coat can be formed by a known method. For example, in addition to coating the surface with a water-repellent or hydrophobic thin film, water-repellent or hydrophilicity can be imparted by arranging a physical shape of the surface. As the former, a hydrophobic film can be formed by applying a highly hydrophobic polymer such as a fluorine-based polymer or a silicone-based polymer in a volatile solvent on a substrate and drying it. As the latter, for example, nano-level unevenness that cannot be soaked with water is provided on the surface to hold an air layer in the uneven portion to impart water repellency, or micron-level grain processing is formed on the surface to increase the hydrophobicity.

During the treatment such as sterilization of the contact lenses 16, 16 with the treatment liquid 12 such as hydrogen peroxide solution, bubbles are generated by the decomposition reaction of the hydrogen peroxide solution. In particular, in the present embodiment, since the catalyst 32 is arranged at the bottom of the storage area 14, the oxygen gas bubbles generated near the bottom effectively agitate the treatment liquid 12 as a whole. Further, by stirring the treatment liquid 12, the contact lenses 16, 16 held in the support portion 50 effectively contact with the treatment liquid 12 through the communication holes 76 of the holder base 70 and the mesh portion 86 of the holder cap 80, whereby the desired treatments such as sterilization is performed.

The foaming of the treatment liquid 12 causes the liquid surface level in the storage area 14 to foam, so that the substantial liquid surface level of the treatment liquid 12 rises. Since the decomposition reaction of the treatment liquid 12 such as hydrogen peroxide solution extends to the liquid surface level raised by the foaming. By setting the upper surface of the bottom wall 66 of the container receiving portion 48 at a position below the maximum level of the liquid surface level fluctuation due to the foaming of the treatment liquid, even if the treatment liquid 12 remains on the upper surface of the bottom wall 66, the decomposition reaction is carried out, and the treatment liquid 12 such as the hydrogen peroxide solution is prevented from being left in the disassembled state.

Figure 9:
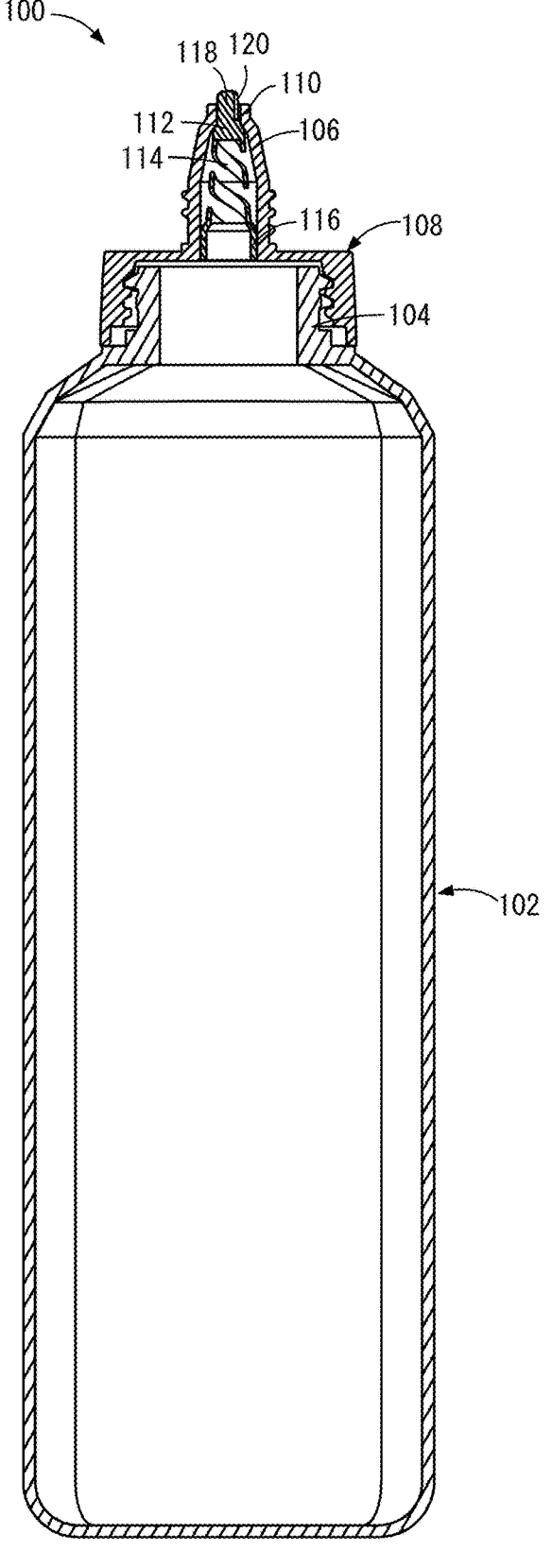
FIG. 9 is a vertical cross sectional view showing an embodiment of a refill container used in combination with the lens case shown in FIG. 1.
Figure 10:
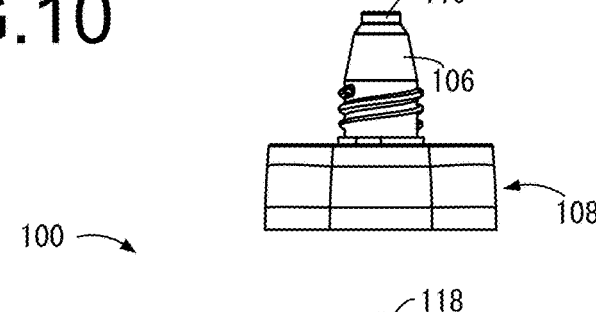
FIG. 10 is an exploded view of the refill container of FIG. 9.
Figure 10:
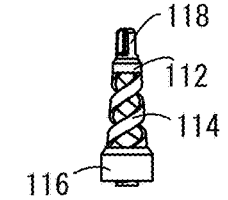
Figure 10:
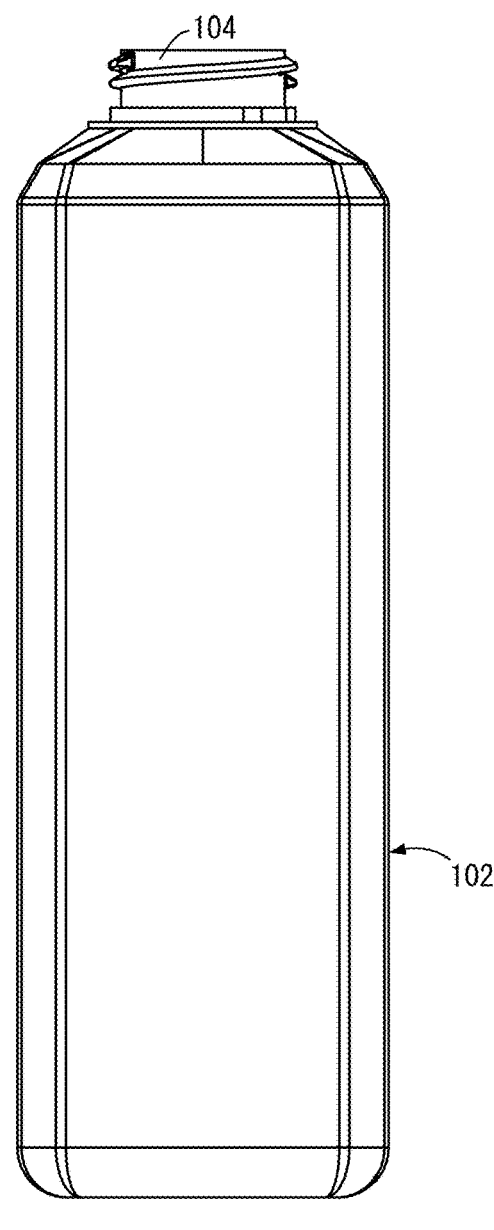

The lens case 10 of the present embodiment is repeatedly used, for example, to disinfect or sterilize a contact lens removed from the eye by a contact lens user. In each of such treatments, the treatment liquid 12 is injected into the case body 18. It is possible to inject an appropriate amount of the treatment liquid 12 into the storage area 14 defined in the lens case 10 with the lid 20 attached to the case body 18 of the lens case 10 to cover the storage recess 22, by using a separate refill container filled with the treatment liquid 12, such as hydrogen peroxide solution. FIGS. 9 and 10 show an embodiment of the refill container.

A refill container 100 may be any as long as it can store the treatment liquid 12 for a long period of time, and the material, shape, structure, capacity, etc. are not limited, but a sufficient capacity is stored while preventing unintended leakage. For example, as shown in the figure, containers with a structure wherein a plug 108 having a spout 106 is fixed to an opening 104 of a bottle body 102 opening upward by welding or screwing, can be adopted.

The refill container 100 of the present embodiment includes the spout 106 having a small diameter and a tapered cylinder shape that protrudes upward from the central portion of the plug 108. A male thread is provided on the outer peripheral surface of the spout 106 so that a cap (not shown) can be attached when the refill container 100 is not used. The spout 106 has an outlet 110 opens at its tip end. Inside the spout 106, a small circular block-shaped valve body 112 serving as a shutoff valve body is provided. The valve body 112 is pressed from the inside against the outlet 110 so as to close the outlet 110.

Figure 11A:
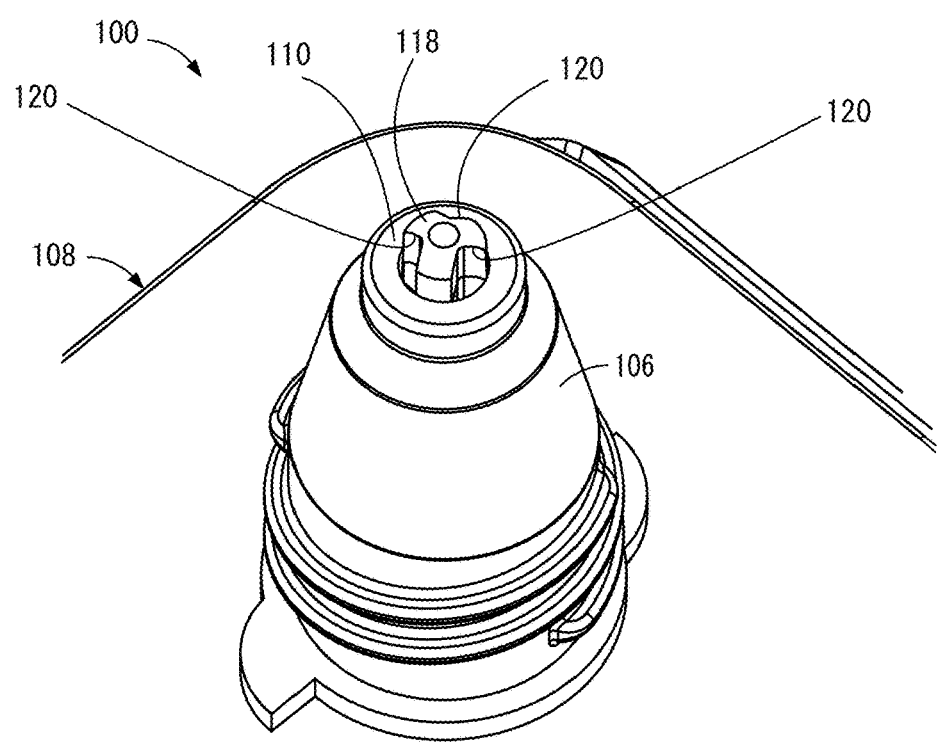
FIGS. 11A and 11B are explanatory views of a nozzle part of the refill container of FIG. 9.
Figure 11B:
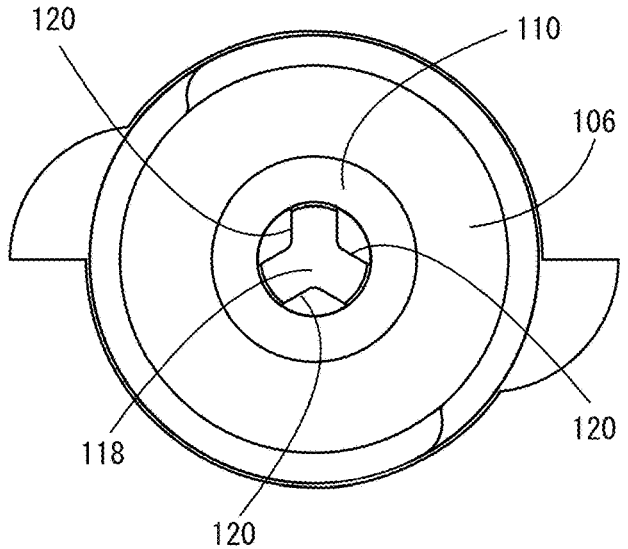
Figure 12A:
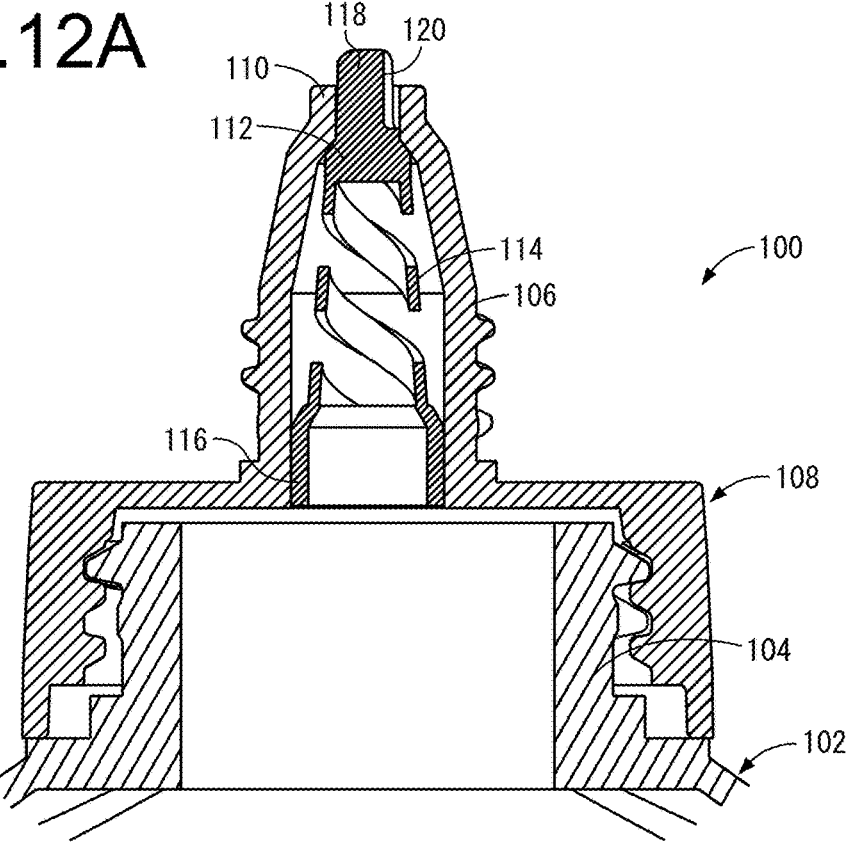
FIGS. 12A and 12B are vertical cross sectional views showing the nozzle part of the refill container of FIG. 9 in a closed state and an open state.
Figure 12B:
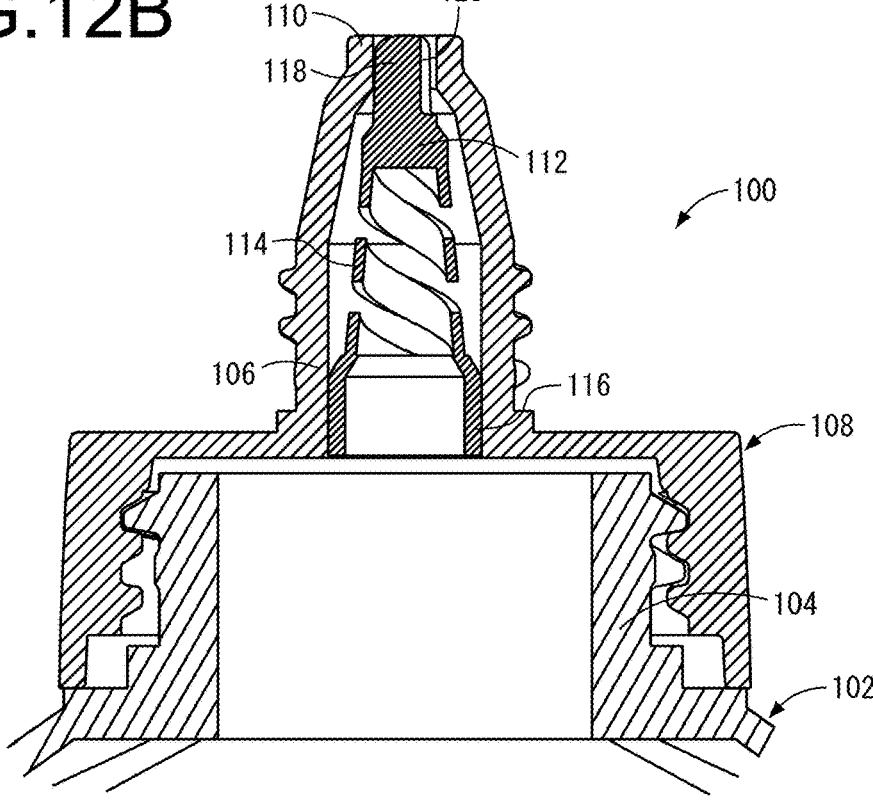

As shown enlarged in FIGS. 11 and 12, the valve body 112 is urged from the inside by a coiled resin spring 114 as an urging means, and is urged from the inside to a tapered or stepped inner peripheral surface at the proximal end side of the circular outlet 110, whereby the outlet 110 can be held in a cutoff state. The resin spring 114 has a tapered double helix structure. The resin spring 114 has a fixing ring 116 that is fitted and fixed to the inner peripheral surface of the spout 106 at the base end portion having a large diameter. The resin spring 114 is integrated with the valve body 112 at the tip portion having a small diameter.

Further, the valve body 112 is provided with an operating protrusion 118 serving as a protrusion that protrudes outward from the central portion, and the operating protrusion 118 is inserted into the outlet 110 of the spout 106 and protrudes outward. As shown in FIG. 11 and the like, the operating protrusion 118 has a size and shape such that a gap extending in the vertical direction is formed between the operating protrusion 118 and the inner peripheral surface of the outlet 110. In the present embodiment, three concave vertical grooves 120 extending in the vertical direction on the outer peripheral surface of the operating protrusion 118 are formed at equal intervals in the circumferential direction, so that the cross-sectional shape of the operating protrusion 118 is substantially radiated. The vertical groove 120 forms a gap extending in the vertical direction in the outlet 110.

By pushing the tip of the operating protrusion 118 protruding outward from the outlet 110, the valve body 112 is moved inward against the urging force of the resin spring 114. With the valve body 112 is moved inward and is separate from the outlet 110, the valve body 112 is switched to the open state.

As a result, the internal space of the refill container 100 is communicated with the outside through the gap between the inner peripheral surface of the outlet 110 and the vertical groove 120 of the operating protrusion 118, and the treatment liquid 12 contained in the refill container 100 is allowed to outflow. When the external force in the pushing direction applied to the tip of the operating protrusion 118 is released, the valve body 112 is pressed against the inner peripheral surface on the base end side of the outlet 110 by the urging force of the resin spring 114 to be in a closed state. As a result of returning and holding, the outlet 110 automatically returns to the cutoff state.

By using the refill container 100 as described above, it is possible to prevent the contained treatment liquid 12 from inadvertently flowing out unless the operating protrusion 118 is pushed in, thereby preventing unintentional scattering of the treatment liquid 12 such as hydrogen peroxide solution. In addition, in the lens case 10 of the present embodiment, a portion where the operating protrusion 118 of the refill container 100 is pushed in to allow the treatment liquid 12 to flow out is specified, whereby scattering of the treatment liquid 12 to the surroundings upon injecting the treatment liquid 12 into the storage container or the like, is more effectively prevented.

Figure 13A:
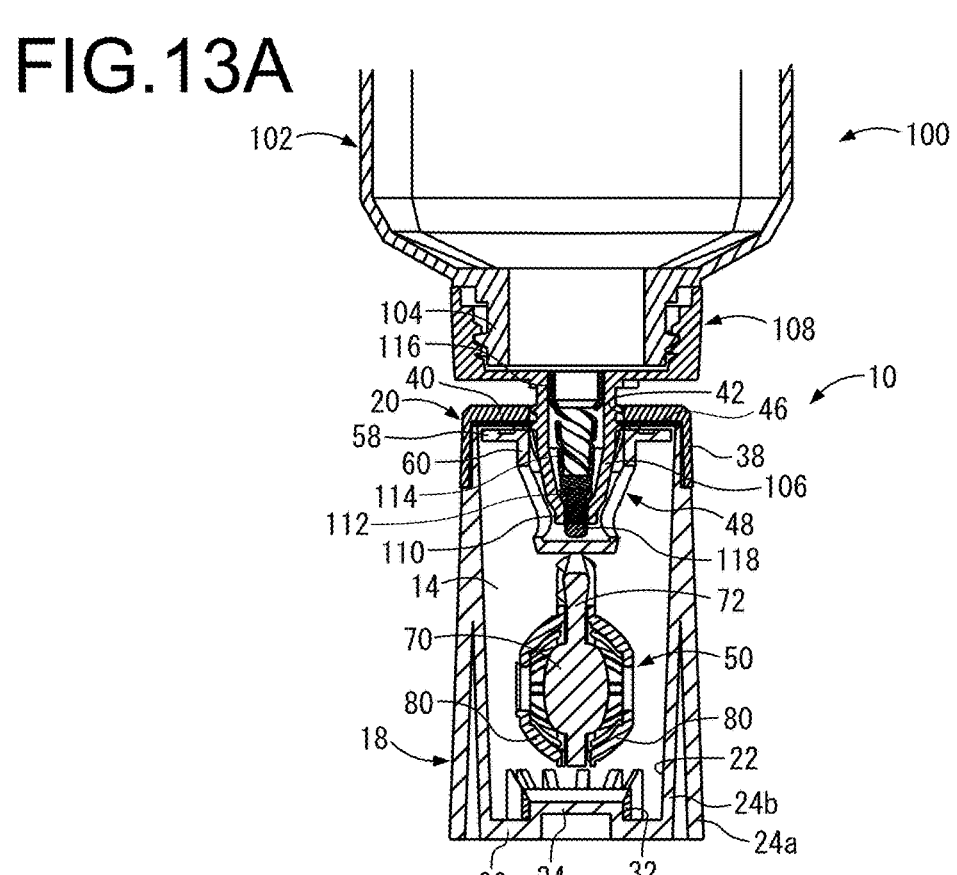
FIGS. 13A and 13B are explanatory views which show nozzle insertion operations upon injecting a treatment liquid into the lens case of FIG. 1 using the refill container of FIG. 9.
Figure 13B:
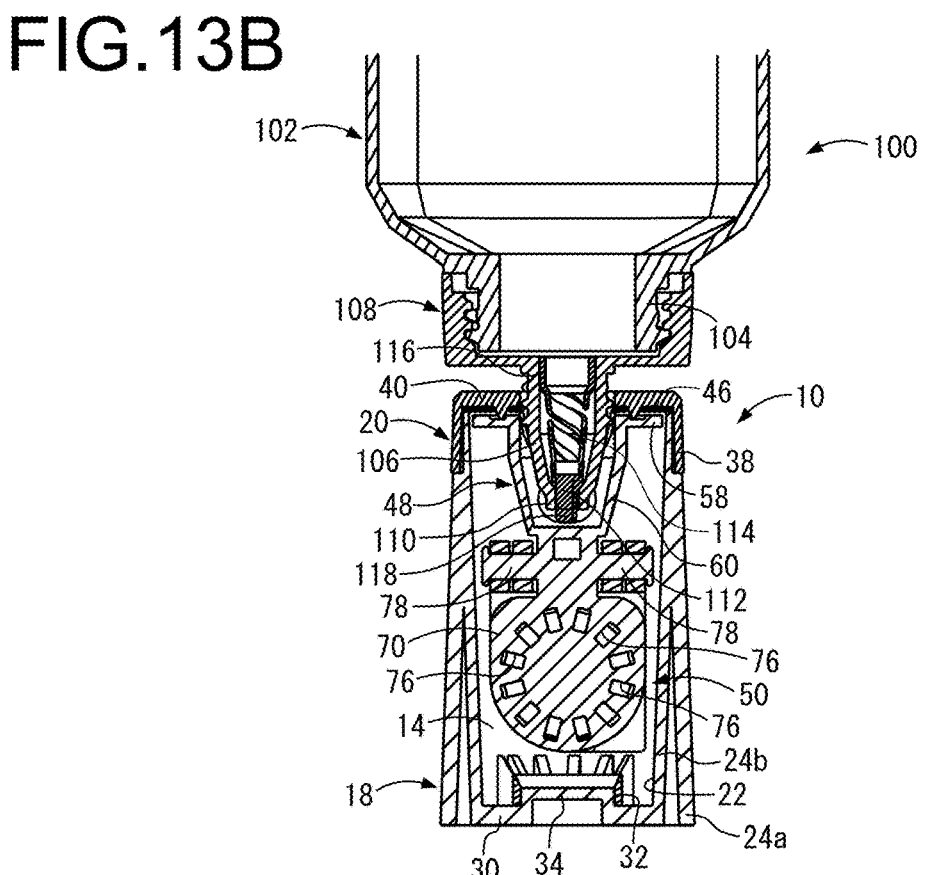

Namely, as shown in FIG. 13, the insertion port 42 formed in the central portion of the lid 20 in the lens case 10 is sized so that the spout 106 of the refill container 100 can be inserted. Then, in an upright state in which the bottom wall 30 of the case body 18 is placed on a horizontal support table or the like, the refill container 100 is turned upside down and the spout 106 directed downward is inserted into the lens case 10 from the insertion port 42 of the lid 20.

Further, the container receiving portion 48 of the lens case 10 has a slightly larger inner peripheral surface shape substantially corresponding to the spout 106 of the refill container 100. Then, the spout 106 inserted from the insertion port 42 of the lid 20 pushes and opens the slit 56 of the packing 46 and enters the container receiving portion 48. At that time, the inner peripheral surface of the insertion port 42 and the container receiving portion 48 is slightly larger than the outer peripheral surface of the spout 106. This generates a guiding action with respect to the spout 106 to be inserted due to direct contact with the spout 106 or contact via the packing 46 with the spout 106, making it possible to avoid a large inclination or catching of the spout 106. In particular, in the present embodiment, the packing 46 made of an elastomer can exert an elastic holding action and/or a sealing action, and the spout 106 of the refill container 100 is further stabilized by the inner peripheral surface of the container receiving portion 48.

Figures 14A, 14B:
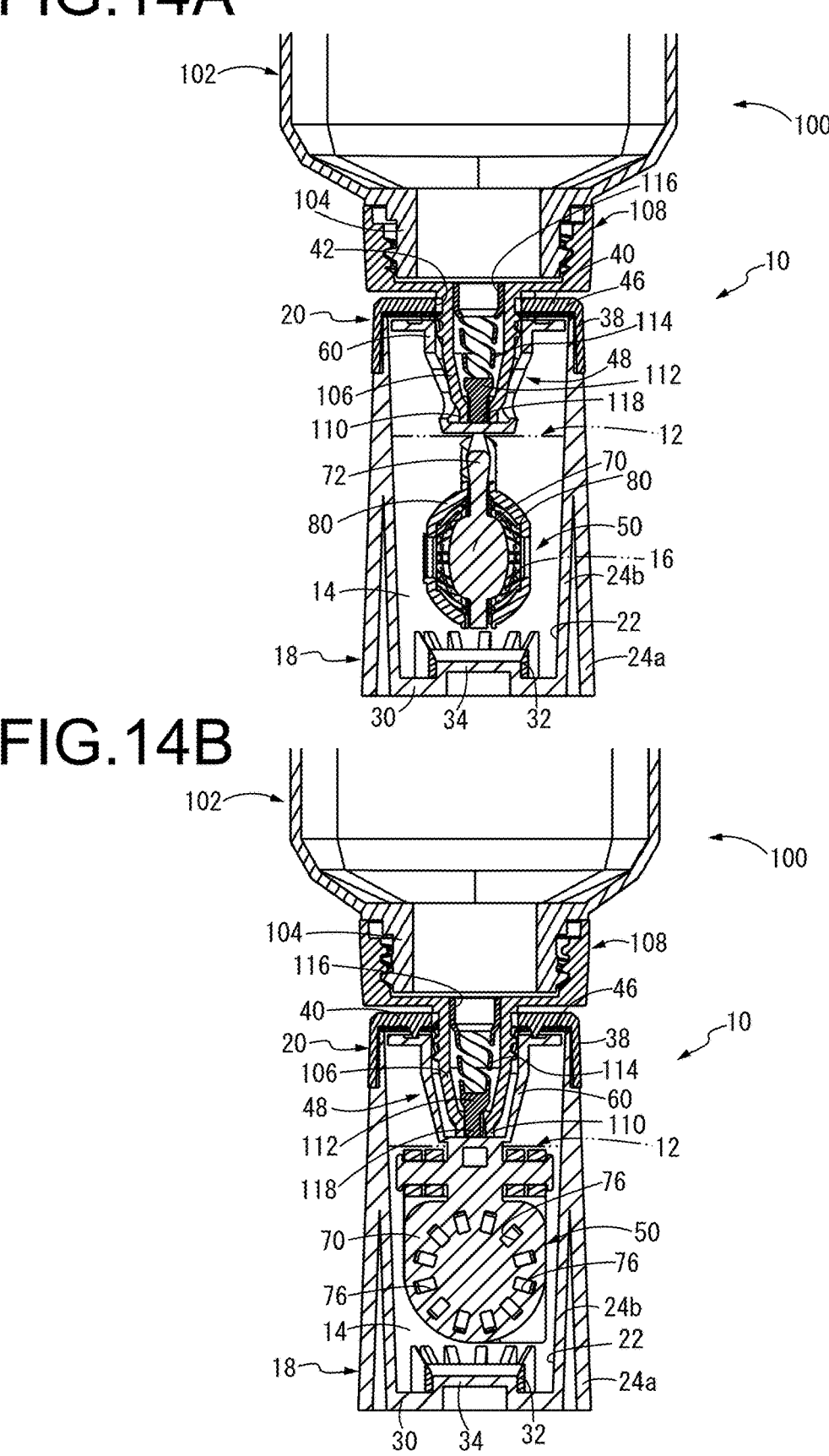
FIGS. 14A and 14B are explanatory views which show nozzle pressing operations upon injecting a treatment liquid into the lens case of FIG. 1 using the refill container of FIG. 9.

When the spout 106 of the refill container 100 is inserted substantially straight into the container receiving portion 48, as shown in FIG. 14, the protruding tip of the operating protrusion 118 protruding from the tip of the spout 106 is brought into contact with the central portion of the bottom wall 66 of the receiving portion 48. Further, the protruding tip of the operating protrusion 118 is pressed against the bottom wall 66 of the container receiving portion 48 due to the weight or operating force of the refill container 100, so that the operating protrusion 118 is pushed inward of the refill container 100.

As a result, the tip of the spout 106 of the refill container 100 abuts directly against the bottom wall 66 of the container receiving portion 48 or indirectly via the operating protrusion 118, and the insertion depth of the spout 106 into the insertion port 42 is limited. The periphery of the spout 106 is also held by the insertion port 42 and the peripheral wall 60 of the container receiving portion 48, so that the spout 106 is positioned with respect to the refill container 100. Under such a state, the operating protrusion 118 is pushed inward of the refill container 100, so that the valve body 112 moves inward, and the closure by the valve body 112 is released and the valve body 112 is set to the open state without any special valve operation. As a result, the treatment liquid 12 contained in the refill container 100 is injected into the lens case 10 from the spout 106 through the gap between the inner peripheral surface of the outlet 110 and the vertical groove 120 of the operating protrusion 118.

In the present embodiment, the bottom wall 66 of the container receiving portion 48 with which the tip end portion of the spout 106 abuts has a lattice structure, and the treatment liquid 12 flowing out from the outlet 110 passes through the lower window 68 of the bottom wall 66 and flows downward where the support portion 50 for the contact lenses 16, 16 is arranged. At that time, the bottom wall 66 of the lattice structure is located below the opening direction of the outlet 110, i.e., a front of the opening direction of the outlet 110, where the flow of the treatment liquid 12 poured from the outlet 110 is large. The bottom wall 66 of the lattice structure constitutes a surface-shielding portion to which the treatment liquid 12 flowing toward the front (downward) in the opening direction hits. By suppressing the momentum of the flow of the treatment liquid 12 poured from the outlet 110 to the storage area 14 by the bottom wall 66 as the surface-shielding portion, the rebound of the treatment liquid 12 can be reduced.

Further, the bottom wall 66 of the lattice structure located immediately in front of the spout 106 in the opening direction also has a substantially triangular cross-sectional shape in which the width dimension gradually decreases toward the upper end facing the spout 106. The rebounding of the treatment liquid 12 due to the bottom wall 66 of the lattice structure is suppressed. If, among the treatment liquids 12 flowing out from the outlet 110, there is a treatment liquid 12 that bounces off the bottom wall 66 or a treatment liquid 12 that cannot completely flow down from the lower window 68 of the bottom wall 66, the treatment liquid 12 can flow into the storage area 14 through the side windows 64 of the peripheral wall 60 of the container receiving portion 48.

That is, the treatment liquid 12 of the refill container 100 is poured out from the outlet 110 of the spout 106 in the container receiving portion 48, and is guided downward through the lower window 68 of the container receiving portion 48 as a guide flow path. The treatment liquid 12 poured from the refill container 100 can be guided into the into the storage area 14, while preventing being scattered to the outer periphery of the lens case 10 by the peripheral wall 60 of the container receiving portion 48, the packing 46, the lid 20 and the like.

Since the spout 106 of the refill container 100 is positioned by the container receiving portion 48, the injection position of the treatment liquid 12 is also stably set to a predetermined position. It is desirable to design that no plane (a plane that spreads in the horizontal direction) that is orthogonal to the vertical direction that is the outflow direction is provided below the outlet 110, i.e., in the opening direction of the outlet 110. As a result, it is possible to more effectively prevent the treatment liquid 12 that has been vigorously flowed downward from the outlet 110 from bouncing upward and leaking to the outside through, for example, a gap in the packing 46.

Therefore, according to a treatment set with an ocular device case including the lens case 10 or the refill container 100 of the present embodiment, it is possible to realize the operation of injecting the treatment liquid 12 into the lens case with less scattering. As a result of preventing scattering when the treatment liquid 12 is injected, the problem that the scattered hydrogen peroxide solution or the like adheres to the fingers and unintentionally irritates the eyes of the lens user is effectively prevented.

In particular, in the present embodiment, the pair of contact lenses 16, 16 are both located below the outlet 110 when the treatment liquid 12 is injected into the lens case 10, and the central axis of the lens is substantially horizontal. Since it is held by the support portion 50 in the facing state, it can be effectively prevented that the injected treatment liquid 12 directly hits the surface of the contact lens 16 and rebounds.

The lens case 10 of the present embodiment has a double wall structure in which the peripheral wall 24 of the case body 18 has a substantially straight cylindrical inner peripheral wall 24*b* and an outer peripheral wall 24*a* extending downward. Excellent stability due to the wide bottom surface when placed on a table or the like can be improved while avoiding an unnecessary increase in the amount of treatment liquid. In particular, a force that pushes the outlet 110 of the refill container 100 downward, when injecting the treatment liquid 12, acts on the container receiving portion 48. Therefore, to improve the stability of the case body 18 when placed on a table or the like, is effective in preventing the lens case 10 from being unintentionally tilted due to tilting in the pressing direction or the like.

In the present embodiment, the refill container 100 with a valve provided with the valve body 112 at the outlet 110 of the spout 106 is adopted. Therefore, when injecting the treatment liquid 12 into the lens case 10 by the refill container 100, even if the refill container 100 is tilted or inverted, the unintended outflow of the treatment liquid 12 can be prevented until the operating protrusion 118 at the tip of the outlet 110 is pressed against the bottom wall 66 of the container receiving portion 48 and pushed inward. Therefore, unintentional spillage or splattering of the treatment liquid during the injection operation of the treatment liquid 12 into the lens case 10 can be prevented more effectively.

Moreover, since the space between the insertion port 42 of the lens case 10 into which the spout 106 of the refill container 100 is inserted and the container receiving portion 48 is also covered with the packing 46. This makes it possible to more effectively prevent the treatment liquid 12 injected from the spout 106 into the container receiving portion 48 from jumping out or leaking to the outside of the lens case 10. Further, the packing 46 makes it possible to expand/contract the opening area of the insertion port 42 based on the elastic deformation action. In a state where the spout 106 of the refill container 100 is not inserted, the packing 46 can provide a function as a valve body that reduces the opening area compared to a state where the spout 106 of the refill container 100 is inserted. That is, in the state where the spout 106 of the refill container 100 is inserted, the packing 46 elastically deforms to open the slit 56 to allow the spout 106 to be inserted, while when the spout 106 is pulled out, the packing 46 is elastically deformed and returns to the original plate shape so as to closes the slit 56. In the state where the slit 56 is closed, the outflow of gas generated by the pressure increase in the storage area 14 due to the decomposition of the hydrogen peroxide solution or the like is allowed through the slit 56, and when the lens case 10 is tilted or falls, it can also exert the effect of suppressing the leakage amount of the treatment liquid 12.

In the lens case 10 of the present embodiment, the treatment liquid 12 can be injected into the storage area 14 in which the catalyst 32 is arranged in a state where the contact lenses 16 and 16 are supported at predetermined positions in the storage area 14. Therefore, at the same time as injecting the treatment liquid 12 into the storage area 14, treatment such as sterilization of the contact lenses 16 and 16 is started, and at the same time, a decomposition reaction or the like by catalytic action of the treatment liquid 12 such as hydrogen peroxide solution is started. Therefore, pre-initiation of the decomposition reaction of the treatment liquid 12 with a catalyst 32 before the insertion of the contact lenses 16 and 16, which may be regarded as a problem when the contact lenses 16 and 16 are inserted into the storage area 14 after the injection of the treatment liquid 12 into the storage area 14 is completed, can also be avoided.

The invention is not limited by the specific description of the above embodiments. For example, the refill container used for injecting the treatment liquid 12 into the lens case 10 is not limited to the refill container 100 of the above-described embodiment, and the valve body 112 may not be provided in the spout 106. The spout 106 of the plug 108 may be provided so as to be inclined with respect to the central axis of the bottle body 102 and to protrude toward, for example, laterally or diagonally upward.

Further, the specific structure, shape, size, etc. of the lens case 10 can be changed. For example, in the above-described embodiment, the storage area 14 having a depth larger than the width is used to hold the contact lens 16 in a substantially vertical state. The storage area having a large width compared to the depth may be adopted. In this case, the contact lens 16 is provided with a convex or concave support surface for supporting the front surface or the rear surface of the lens from below in a state where the optical axis of the contact lens 16 is substantially in the vertical direction, and the contact lens 16 is held in a flat state. In each of such embodiments, the container receiving portion and the contact lens support portion do not need to be integrally provided on the lid, and the container receiving portion and the contact lens support portion are also separated. For example, the container receiving portion may be provided on the lid side, while the support portion of the contact lens may be provided on the container body side.

In the above embodiment, the spout 106 of the refill container 100 is inserted through the insertion port 42 of the lid 20, and the treatment liquid 12 is injected into the storage area 14. It is also possible to provide a container receiving portion that allows injection into the storage area from the spout at a place different from the lid. Specifically, for example, a container receiving portion that allows injection of the treatment liquid may be provided at a position of the case body that is offset from the mounting position of the lid to the side or downward. Further, the injection port of the refill container may be inserted from the side into the case body or the lid. In addition to the mode in which treatment liquid is poured into the storage area with the lid attached to the case body and the storage area is closed, for example, the support portion of the contact lens and the container receiving portion are provided separately from the lid. Therefore, it is also possible to adopt a mode in which the treatment liquid is injected into the storage area in which the contact lens is accommodating and supported without the lid being attached. It is also possible to adopt a container receiving portion that appears with the lid member open. Further, it is also possible to adopt a mode in which the treatment liquid can be poured into the storage area in which the contact lens is supported in the state where the lid is closed by the lid of the case body without providing the container receiving portion for receiving the spout of the refill container.

In the illustrated embodiment, the refill container 100 employs the structure in which the outlet 110 is opened by pressing the operating protrusion 118 against the container receiving portion 48 of the lens case 10 and pushing it inward. Alternatively, various valve means that are opened by contact with respect to the lens case or the like can be adopted. Specifically, as described in Japanese Unexamined Patent Publication No. JP-A-2004-290473, an elastic valve with a slit is attached to the outlet, and a male luer-shaped hollow pin is provided so as to project from the container receiving portion of the contact lens case. The elastic valve may be opened by inserting it into the slit of the elastic valve.

In addition, it is possible to set a shape and color that makes it easy to pay attention to the insertion port where the spout of the refill container is inserted in the lens case, so that the user can pay attention to the insertion port and the insertion port can be more distinct.

The container receiving portion to which the spout of the refill container is brought into contact is not limited to the bottomed tubular shape as described above. For example, if the spout of the refill container does not have a valve means that opens by pressing, it is also possible to form a container receiving portion into a cylindrical shape or an arc shape without a bottom, thereby exerting a positioning action in a specific direction by abutting the spout of the refill container with the container receiving portion.

The treatment liquid 12 is not limited to ones of the illustrated embodiment, and may be used for storage treatment, disinfection, cleaning and the like of an ocular device such as a contact lens 16. For example, adaptable treatment liquid may include any of a peroxide selected from hydrogen peroxide, perboric acid, peracetic acid, performic acid, and salts thereof, or an oxide of chlorine selected from chlorine dioxide, chlorite, hypochlorite, and salts thereof, or povidone-iodine. The catalyst 32 illustrated in the embodiments is also used as appropriate for the treatment liquid 12, and the presence or absence and type of catalyst 32 is not limited. For example, in addition to the catalyst such as platinum illustrated for the treatment liquid of hydrogen peroxide water, tablets of enzymes such as catalase can also be employed. In this case, for example, the tablets can be introduced into the case body before injection of the treatment liquid. When using, for example, a povidone-iodine disinfectant other than hydrogen peroxide water as the treatment liquid 12, it is also possible to employ neutralizing tablets such as sodium sulfite or ascorbic acid.

As described above, the scope of the present invention is not limited to the case for the exemplary contact lens, the processing set, and the like. In addition to cases for various contact lenses such as vision correction contact lenses, beauty contact lenses, special contact lenses, functional contact lenses, and treatment liquid sets with cases, the present invention can apply to cases or treatment liquid sets with cases for storing and transferring intraocular lenses. In addition, an ocular device case can be integrally or additionally provided with other functional means, for example: a timer for measuring the processing time and the like; a display means for showing processing status by light, sound, or the like; and a sensor or a monitor for measuring the degree of dirt on the ocular device or confirming damage such as chipping. The present invention can also be effectively applied to an ocular device case or a treatment liquid set provided with such functional means. Furthermore, the specific shape and size of the case can be appropriately changed depending on the lens or the like to which the invention is applied. The present invention can also be applied to a case used for a single or three or more ocular devices.

KEYS TO SYMBOLS

10 lens case
12 treatment liquid
14 storage area
16 contact lens
18 case body
20 lid
22 storage recess
24 peripheral wall (outer peripheral wall 24a, inner peripheral wall 24b)
26 stepped surface
28 lid fitting portion
30 bottom wall
32 catalyst
34 inward convex portion
36 opening
38 peripheral wall (outer peripheral wall 38a, inner peripheral wall 38b)
40 upper bottom wall
42 insertion port
44 fixing protrusion
46 packing
48 container receiving portion
50 supporting portion
52 holder member with receiving portion
54 positioning hole
56 slit
58 flange-shaped portion
60 peripheral wall
62 peripheral groove
64 side window
66 bottom wall
68 lower window
70 holder base
72 connecting part
74 holding convex portion
76 communication hole
78 support shaft
80 holder cap
82 hook
86 mesh portion
88 annular plate portion
92 prescript liquid surface level
100 refill container
102 bottle body
104 opening
106 spout
108 plug
110 outlet
112 valve body
114 resin spring
116 fixing ring

23

118 operating protrusion

120 vertical groove

The invention claimed is:

1. An ocular device case for use by injecting a treatment liquid from a separate refill container, the ocular device case comprising:

a case body having a storage area for the treatment liquid and configured to store an ocular device;

a lid attached to an opening of the storage area in the case body;

a container receiving portion configured to contact a spout of the refill container to allow the treatment liquid to be injected into the storage area; and an insertion port configured to have the spout of the refill container inserted into the insertion port, wherein the container receiving portion is inward of the insertion port such that the container receiving portion projects from the insertion port into an inside of the storage area, the ocular device case is configured to removably insert an ocular device, and the container receiving portion is arranged to contact the spout of the refill container from above and pour the treatment liquid from the separate refill container into the storage area.

2. The ocular device case according to claim 1, further comprising a support portion for supporting the ocular device in the storage area.

3. The ocular device case according to claim 1, wherein the container receiving portion is arranged to contact the spout of the refill container pointed downward from above in an upright state of the case body while the lid is attached.

4. The ocular device case according to claim 1, wherein the container receiving portion is configured such that an insertion depth of the spout of the refill container with respect to the insertion port is configured to be limited by a contact of a tip of the spout of the refill container with the container receiving portion.

5. The ocular device case according to claim 1, wherein the container receiving portion and the storage area are configured such that a contact position of a tip of the spout of the refill container configured to be positioned in the container receiving portion is above a prescript position of a liquid surface level of the treatment liquid in the storage area.

6. The ocular device case according to claim 1, further comprising the ocular device supported in the storage area by a support portion, and an agent acting on the treatment liquid in the storage area of the case body, wherein the lid is attached.

7. The ocular device case according to claim 1, wherein the container receiving portion comprises a guide flow path configured to guide the treatment liquid injected from the spout downward from a contact position of a tip of the spout of the refill container.

8. The ocular device case according to claim 1, wherein a surface of the container receiving portion is coated with a water-repellent or hydrophobic surface coat.

9. The ocular device case according to claim 1, further comprising the treatment liquid, wherein the treatment liquid is for disinfecting or cleaning the ocular device and comprises any one of the following:

a peroxide selected from hydrogen peroxide, perboric acid, peracetic acid, performic acid, and salts thereof;

an oxide of chlorine selected from chlorine dioxide, chlorite, hypochlorite, and salts thereof; and Povidone Iodine.

10. The ocular device case according to claim 1, further comprising the ocular device, wherein the ocular device is at least one of a contact lens for vision correction of at least one of myopia, hyperopia, and presbyopia;

a cosmetic contact lens for at least one of iris coloring and limbal dilation;

a myopia suppression contact lens, an orthokeratology contact lens;

a contact lens for conical corneal;

a functional contact lens equipped with at least one of sensors, communication functions, and imaging functions;

a non-crystal intraocular lens; and a crystal intraocular lens.

11. A combination of the ocular device case according to claim 1 and the refill container, the refill container comprising:

the treatment liquid, the spout through which the treatment liquid flows out; and a shutoff valve body having a protrusion protruding outward from a tip of the spout, wherein the shutoff valve body is in the spout such that the shutoff valve body is urged from an inside toward an outside of the spout with the protrusion protruding outward to block the spout, and with the protrusion at the spout being brought into contact with the container receiving portion of the ocular device case and pushed inward, the spout opens to allow the treatment liquid to flow out from the spout.

12. An ocular device case for use by injecting a treatment liquid from a separate refill container, the ocular device case comprising:

a case body having a storage area for the treatment liquid and configured to store an ocular device removed by a user;

a lid attached to an opening of the storage area in the case body, and a support portion for supporting the ocular device in the storage area, the support portion being attached to the lid, wherein an entirety of the lid is configured to be removably attachable to the case body, and the ocular device case is configured to allow pouring the treatment liquid into the storage area in a state where the lid is mated to the case body.

13. An ocular device case for use by injecting a treatment liquid from a separate refill container, the ocular device case comprising:

a case body having a storage area for the treatment liquid and configured to store an ocular device;

a lid attached to an opening of the storage area in the case body;

a container receiving portion configured to contact a spout of the refill container to allow the treatment liquid to be injected into the storage area; and an insertion port configured to have the spout of the refill container inserted into the insertion port, a holder cap in direct contact with the container receiving portion and configured to be removable from the case body and further configured to submerge the ocular device in the storage area, wherein the container receiving portion is inward of the insertion port such that the container receiving portion projects from the insertion port into an inside of the storage area, and the ocular device case is configured to removably insert an ocular device.

14. An ocular device case for use by injecting a treatment liquid from a separate refill container, the ocular device case comprising:

a case body having a storage area for the treatment liquid and configured to store an ocular device removed by a user;

a lid attached to an opening of the storage area in the case body, a holder cap within the case body and configured to be removable from the case body and further configured to submerge the ocular device in the storage area, wherein an entirety of the lid is configured to be removably attachable to the case body, and the ocular device case is configured to allow pouring the treatment liquid into the storage area in a state where the lid is mated to the case body.

\* \* \* \* \*